United States Patent
Sancoff et al.

(10) Patent No.: US 6,682,540 B1
(45) Date of Patent: Jan. 27, 2004

(54) APPARATUS AND METHOD FOR PLACING MULTIPLE SUTURES

(75) Inventors: Gregory E. Sancoff, North Hampton, NH (US); John T. Rice, Lincoln, MA (US); Frederic P. Field, North Hampton, NH (US)

(73) Assignee: Onux Medical, Inc., Hampton, NH (US)

( * ) Notice: Subject to any disclaimer, the term of this patent is extended or adjusted under 35 U.S.C. 154(b) by 343 days.

(21) Appl. No.: 09/705,997

(22) Filed: Nov. 3, 2000

Related U.S. Application Data

(60) Provisional application No. 60/163,680, filed on Nov. 5, 1999.

(51) Int. Cl.[7] .............................................. A61B 17/08
(52) U.S. Cl. ....................................................... 606/153
(58) Field of Search ................................ 606/139, 153, 606/152, 151, 144, 194, 198, 155, 156, 154, 158; 623/23.64, 1.1, 1.36

(56) References Cited

U.S. PATENT DOCUMENTS

| | | | |
|---|---|---|---|
| 4,214,587 A | | 7/1980 | Sakura, Jr. |
| 4,366,819 A | | 1/1983 | Kaster |
| 4,553,543 A | | 11/1985 | Amarasinghe |
| 4,957,499 A | * | 9/1990 | Lipatov et al. .............. 606/153 |
| 5,104,399 A | | 4/1992 | Lazarus |
| 5,122,156 A | | 6/1992 | Granger et al. |
| 5,234,447 A | | 8/1993 | Kaster et al. |
| 5,336,233 A | * | 8/1994 | Chen .......................... 606/153 |
| 5,489,295 A | | 2/1996 | Piplani et al. |
| 5,562,728 A | | 10/1996 | Lazarus et al. |
| 5,695,504 A | | 12/1997 | Gifford, III et al. |
| 5,720,776 A | | 2/1998 | Chuter et al. |
| 5,749,920 A | | 5/1998 | Quiachon et al. |
| 5,755,778 A | | 5/1998 | Kleshinski |
| 5,800,526 A | | 9/1998 | Anderson et al. |
| 5,843,164 A | | 12/1998 | Frantzen et al. |
| 5,843,167 A | | 12/1998 | Dwyer et al. |
| 5,843,170 A | | 12/1998 | Ahn |
| 5,921,995 A | | 7/1999 | Kleshinski |
| 5,941,908 A | | 8/1999 | Goldsteen et al. |
| 5,954,735 A | | 9/1999 | Rygaard |
| 6,001,124 A | | 12/1999 | Bachinski |
| 6,004,347 A | | 12/1999 | McNamara et al. |
| 6,030,392 A | * | 2/2000 | Dakov ......................... 606/139 |
| 6,113,612 A | | 9/2000 | Swanson et al. |
| 6,152,937 A | | 11/2000 | Peterson et al. |
| 6,187,020 B1 | * | 2/2001 | Zegdi et al. .................. 606/153 |
| 6,193,734 B1 | * | 2/2001 | Bolduc et al. ............... 606/153 |
| 6,506,210 B1 | * | 1/2003 | Kanner ........................ 606/213 |

FOREIGN PATENT DOCUMENTS

| WO | WO 98/19629 A3 | 5/1998 |
|---|---|---|
| WO | WO 98/19629 A2 | 5/1998 |
| WO | WO 98/19634 A2 | 5/1998 |
| WO | WO 98/19634 A3 | 5/1998 |
| WO | WO 99/62415 A1 | 12/1999 |

* cited by examiner

*Primary Examiner*—A. Vanatta
(74) *Attorney, Agent, or Firm*—Pandiscio & Pandiscio

(57) ABSTRACT

An apparatus for placing multiple sutures during anastomosis of physiological vessels includes a crown portion having a plurality of strands connected together by one or more circular bands. The strands each form a point at one end with a curved hook at the same end. The curved hook acts as a suture to retain one or more of the vessels. An alternative embodiment includes a plurality of strands, or wires, that are inserted through one or more vessels to simultaneously place multiple sutures. The present invention also comprises a method for placing a plurality of sutures simultaneously with an apparatus.

14 Claims, 38 Drawing Sheets

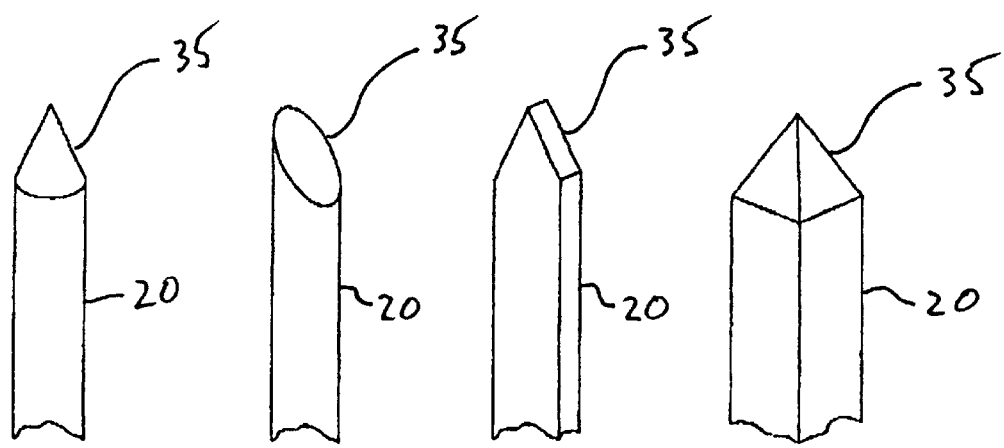

External Version of Crown

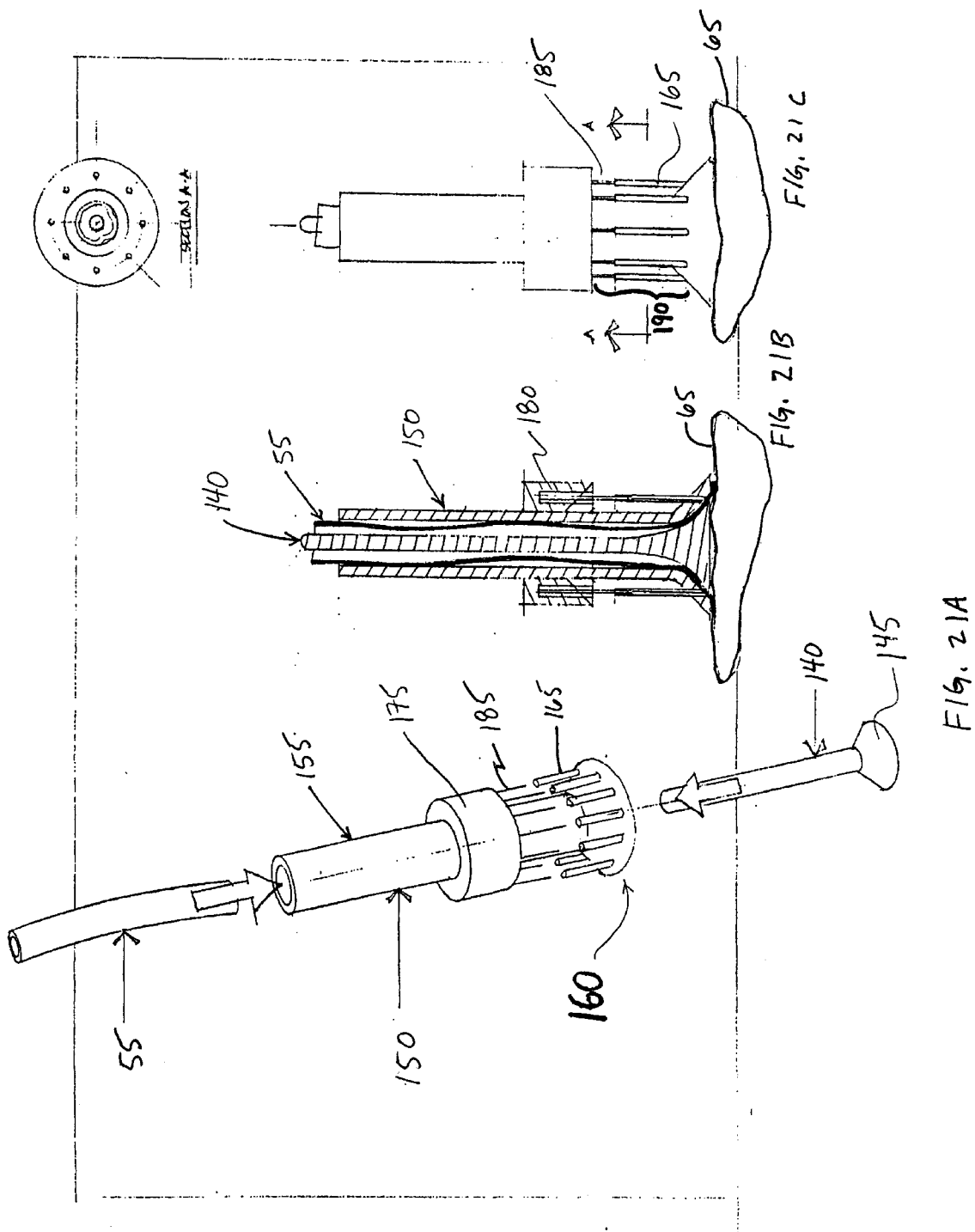

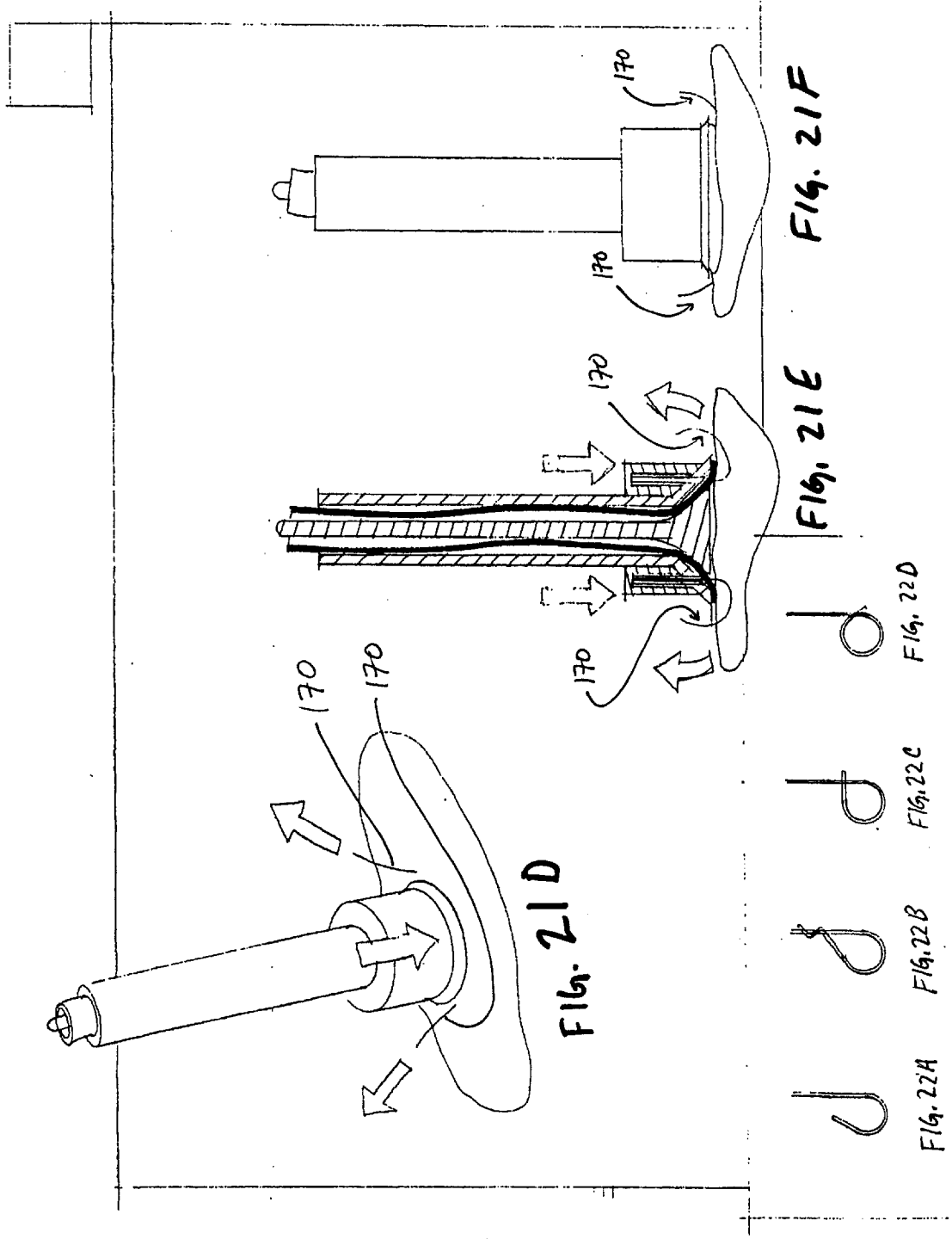

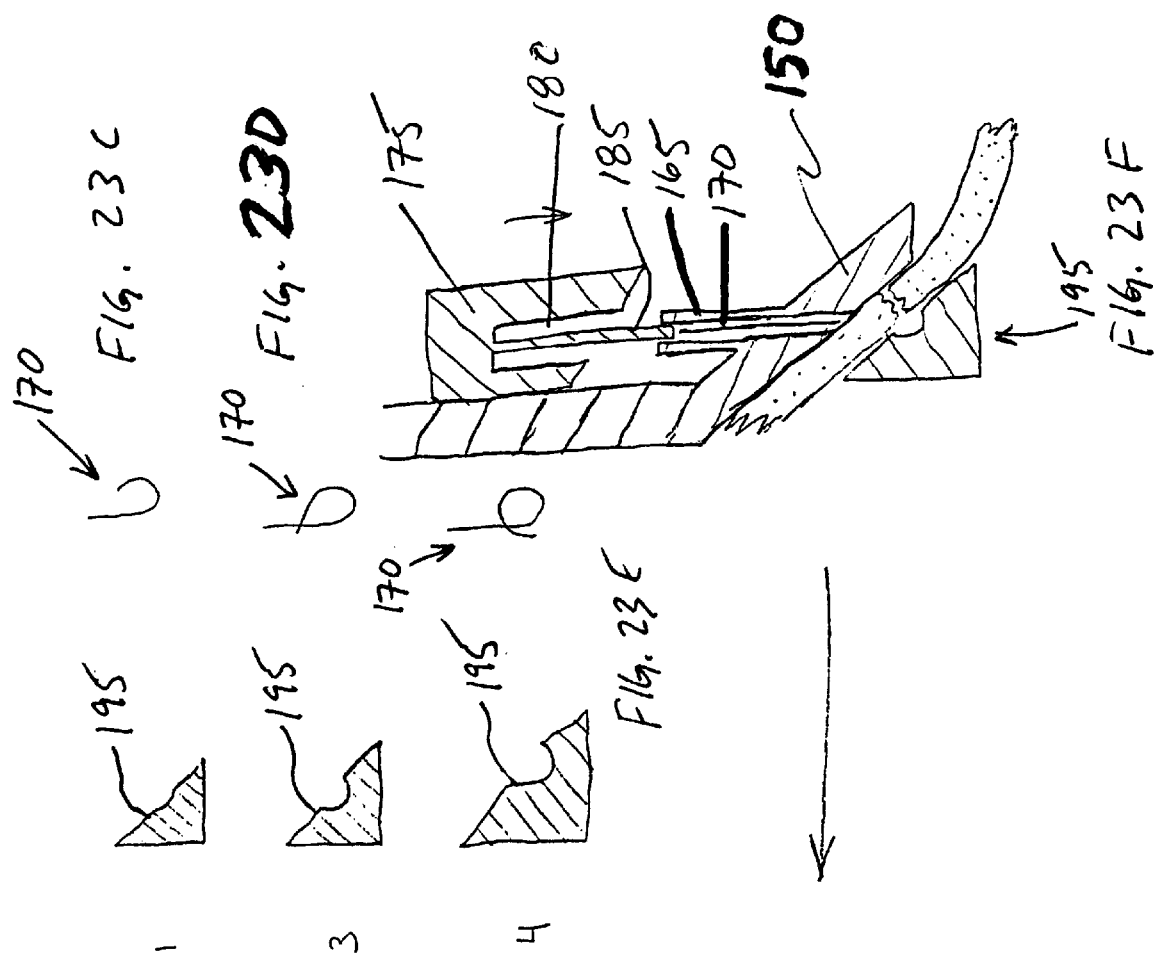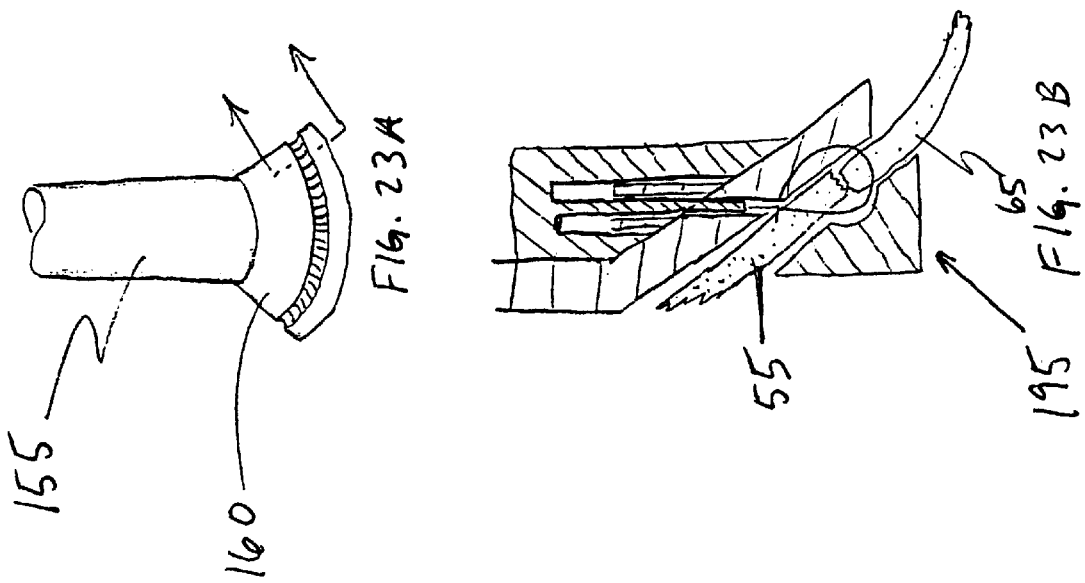

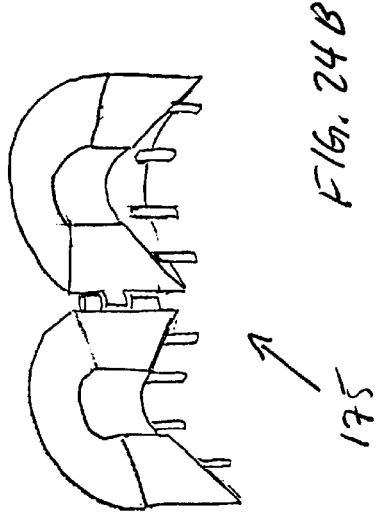
FIG. 24B
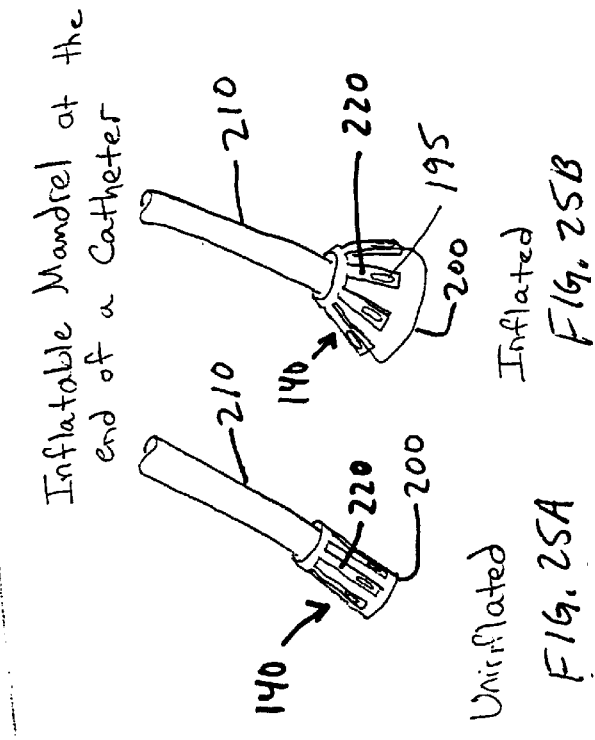
Inflatable Mandrel at the end of a Catheter
FIG. 25A Uninflated
FIG. 25B Inflated
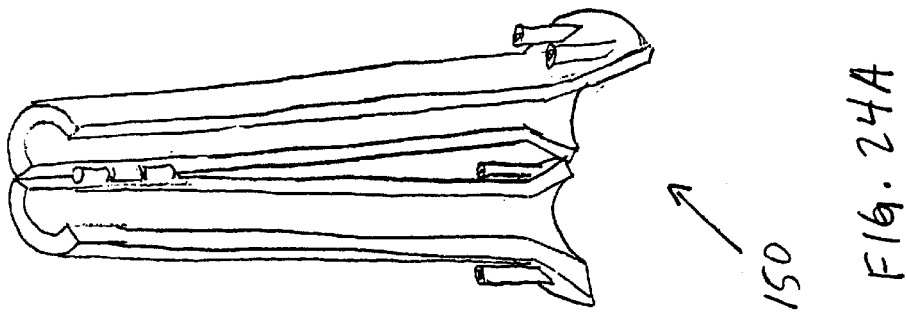
FIG. 24A

APPARATUS AND METHOD FOR PLACING MULTIPLE SUTURES

REFERENCE TO EARLIER APPLICATION

This application claims the benefit of pending U.S. Provisional Patent Application Ser. No. 60/163,680, filed Nov. 5, 1999 by Gregory E. Sancoff, John T. Rice and Frederic P. Field. The aforementioned document is incorporated herein by reference.

FIELD OF THE INVENTION

The invention generally relates to apparatus and methods for surgery. More specifically, the invention relates to apparatus and methods for the surgical formation of anastomosis of physiological vessels.

BACKGROUND OF THE INVENTION

It is a common surgical procedure to join together two or more physiological vessels, such as intestines or blood vessels. The three main types of connections include: end-to-end, end-to-side, and side-to-side connections. As these structures often carry fluid, the connections formed must be at least substantially complete around the entire surface. Traditional means for connecting together these structures include the use of sutures or staples.

Placing sutures by hand around the circumference of a vessel is often very difficult and cumbersome due to various factors. These factors include space limitations at the typical surgical site and attachment of the desired surgical vessel to or containment within various other structures. Such limitations impede manipulation and cause difficulty in accessing remote sides of the desired surgical vessels.

Additionally, blood vessels such as the coronary arteries, or those vessels used to form bypasses, are small in diameter and have very thin walls. The thin walls cause these vessels to adopt a collapsed configuration during handling which causes difficulty in handling and positioning the vessels.

An object of the invention is to provide an apparatus for placing multiple sutures during anastomosis of physiological vessels.

Another object of the invention is to provide a method for placing multiple sutures during anastomosis of physiological vessels.

SUMMARY OF THE INVENTION

An apparatus for placing multiple sutures during anastomosis of physiological vessels includes a crown portion having a plurality of strands connected together by one or more circular bands. The strands each form a point at one end with a curved hook at the same end. The curved hook acts as a suture to retain one or more of the vessels.

An alternative embodiment includes a plurality of strands, or wires, that are inserted through one or more vessels to simultaneously place multiple sutures.

The present invention also comprises a method for placing a plurality of sutures simultaneously with an apparatus.

BRIEF DESCRIPTION OF THE DRAWINGS

FIGS. 16–19 illustrate various pointed ends of a strand.

FIGS. 21A–21F illustrate a device that places and secures sutures for making anastomotic connections.

FIGS. 22A–22D illustrate various wire end configurations.

FIGS. 23A–23F illustrate various die surface embodiments of a device that places and secures sutures for making anastomotic connections.

FIGS. 24A–24B illustrate embodiments of a hinged device that places and secures sutures for making anastomotic connections.

FIGS. 25A–25B illustrate an inflatable mandrel at the end of a catheter for a device that places and secures sutures for making anastomotic connections.

DETAILED DESCRIPTION OF THE PREFERRED EMBODIMENTS

Figure 1A:
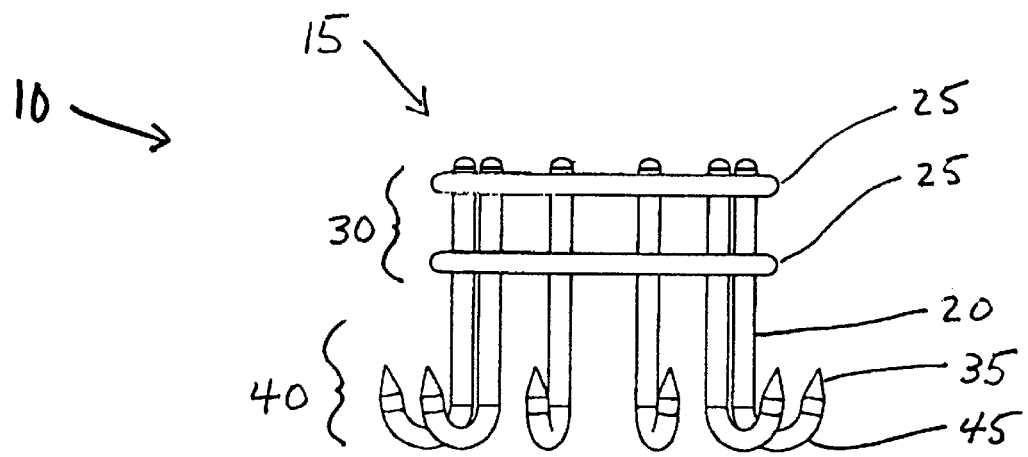
FIGS. 1A–1E illustrate an embodiment of a crown for placing multiple sutures.
Figure 1B:
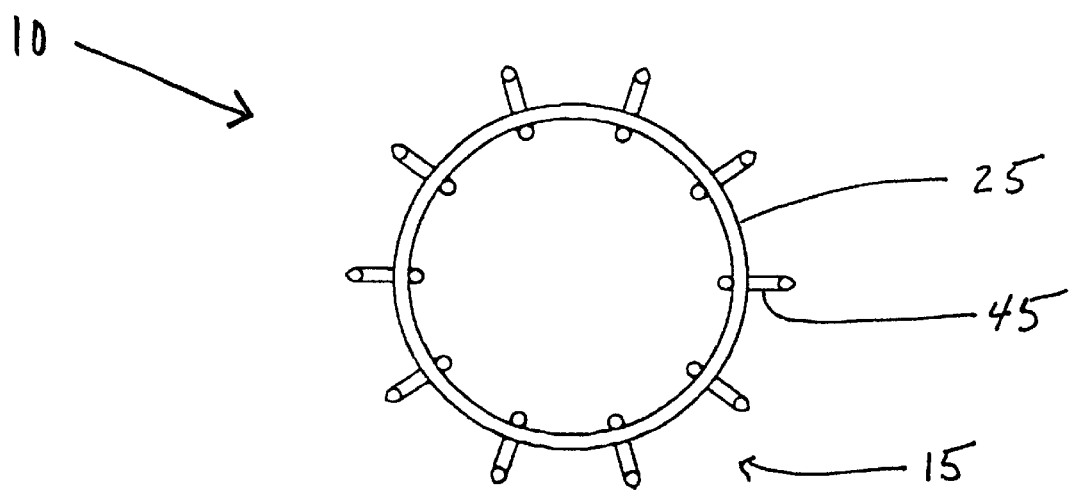
Figure 1C:
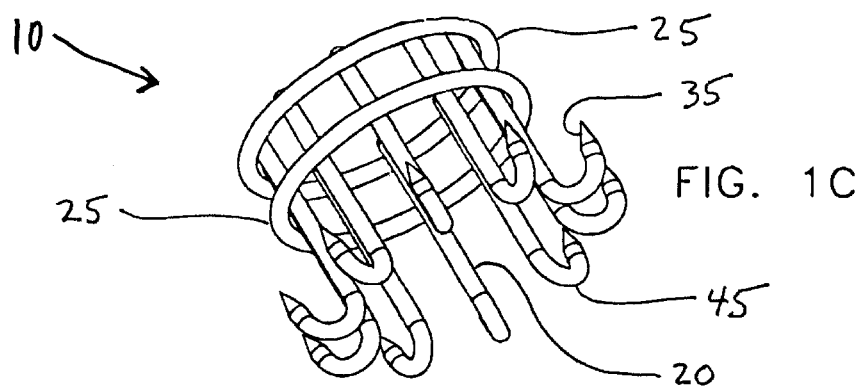
Figure 1D:
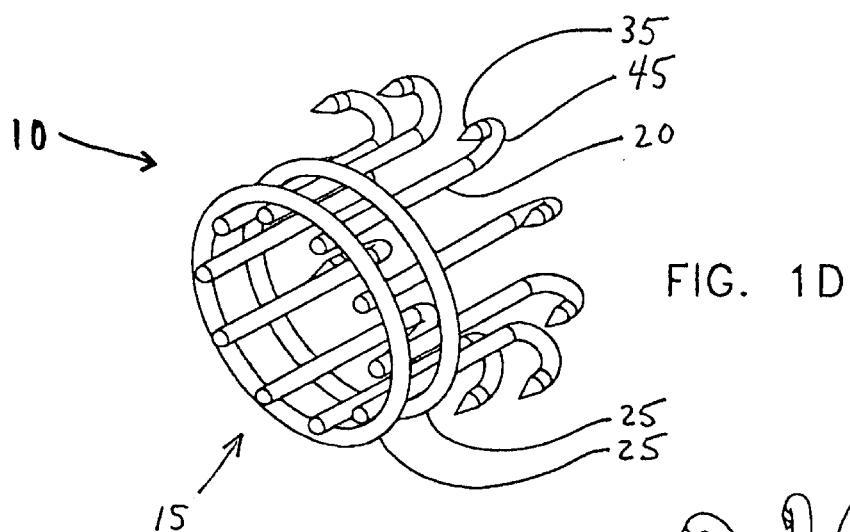
Figure 1E:
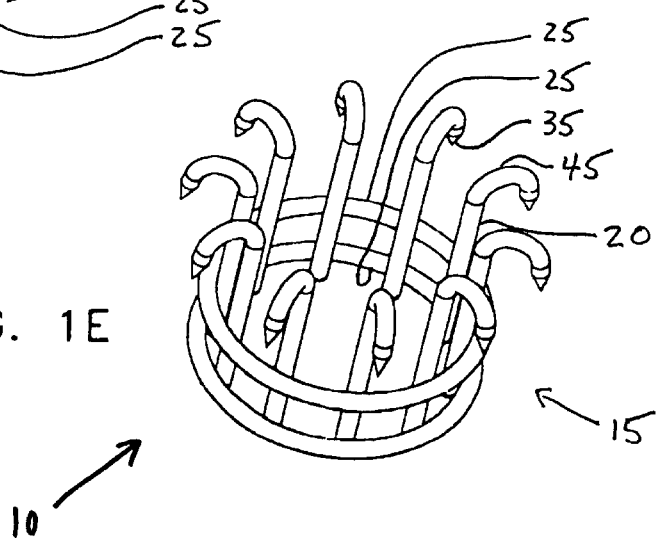
Figure 2A:
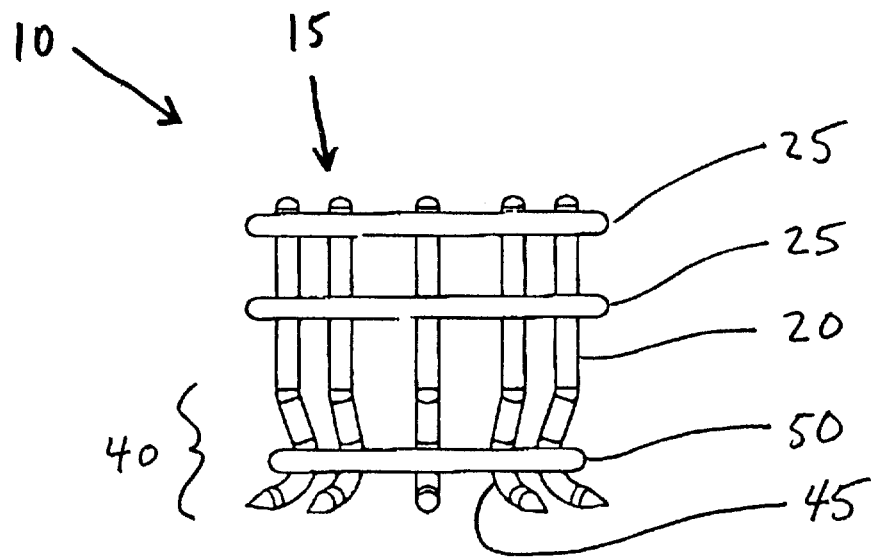
FIGS. 2A–2D illustrate a crown including a retaining ring.
Figure 2B:
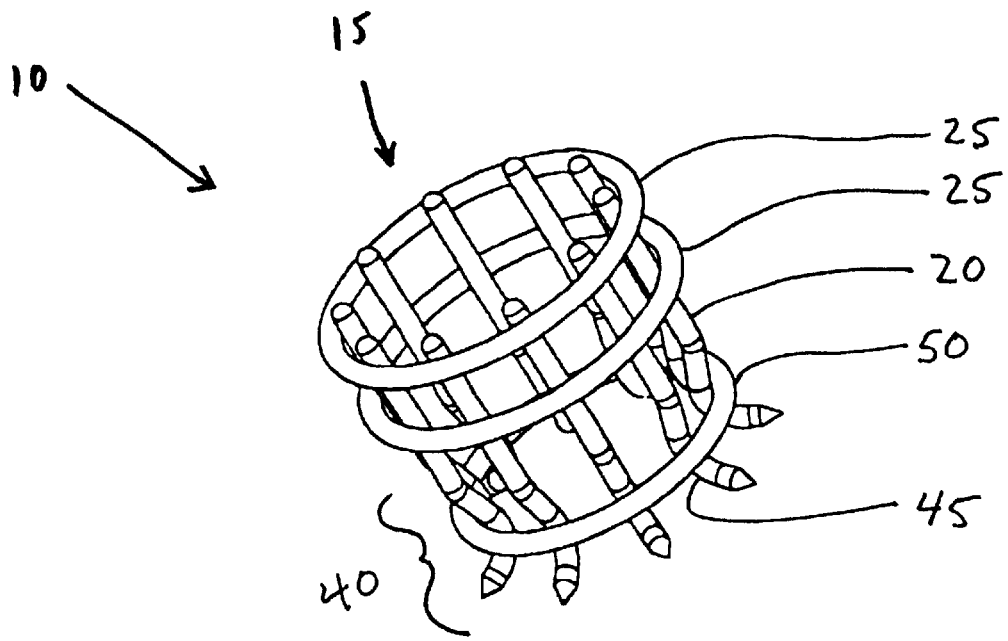
Figure 2C:
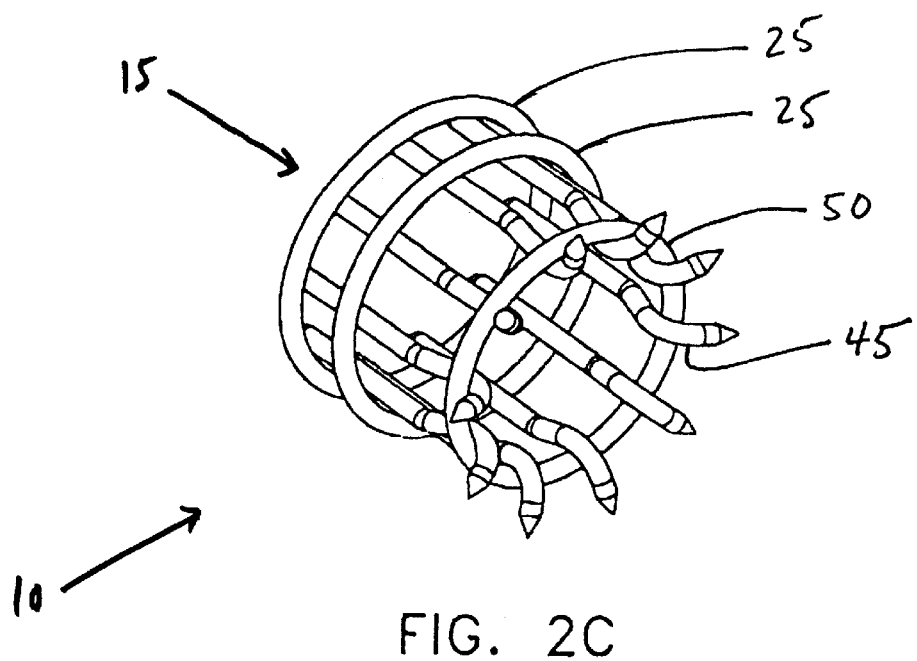
Figure 2D:
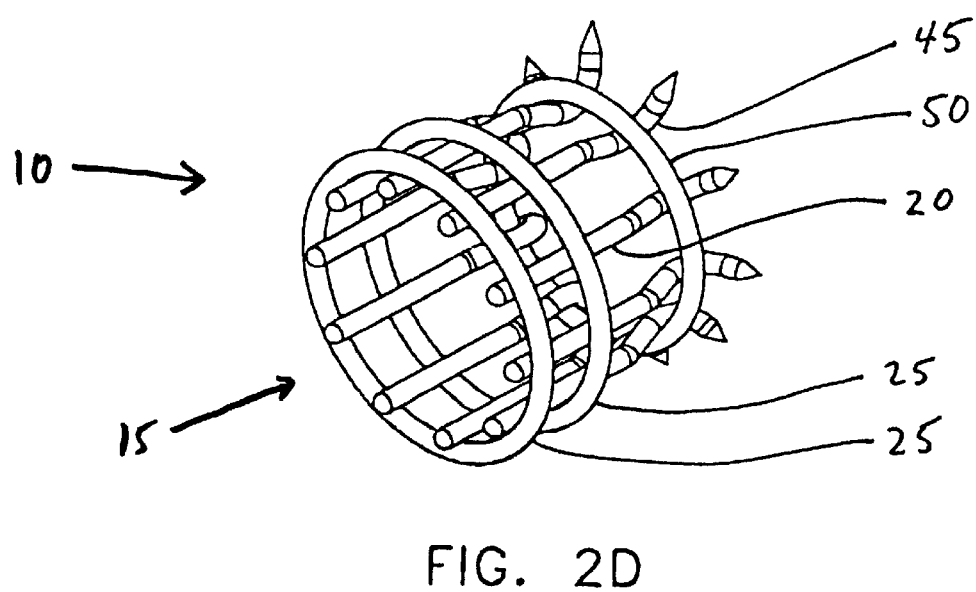
Figure 3:
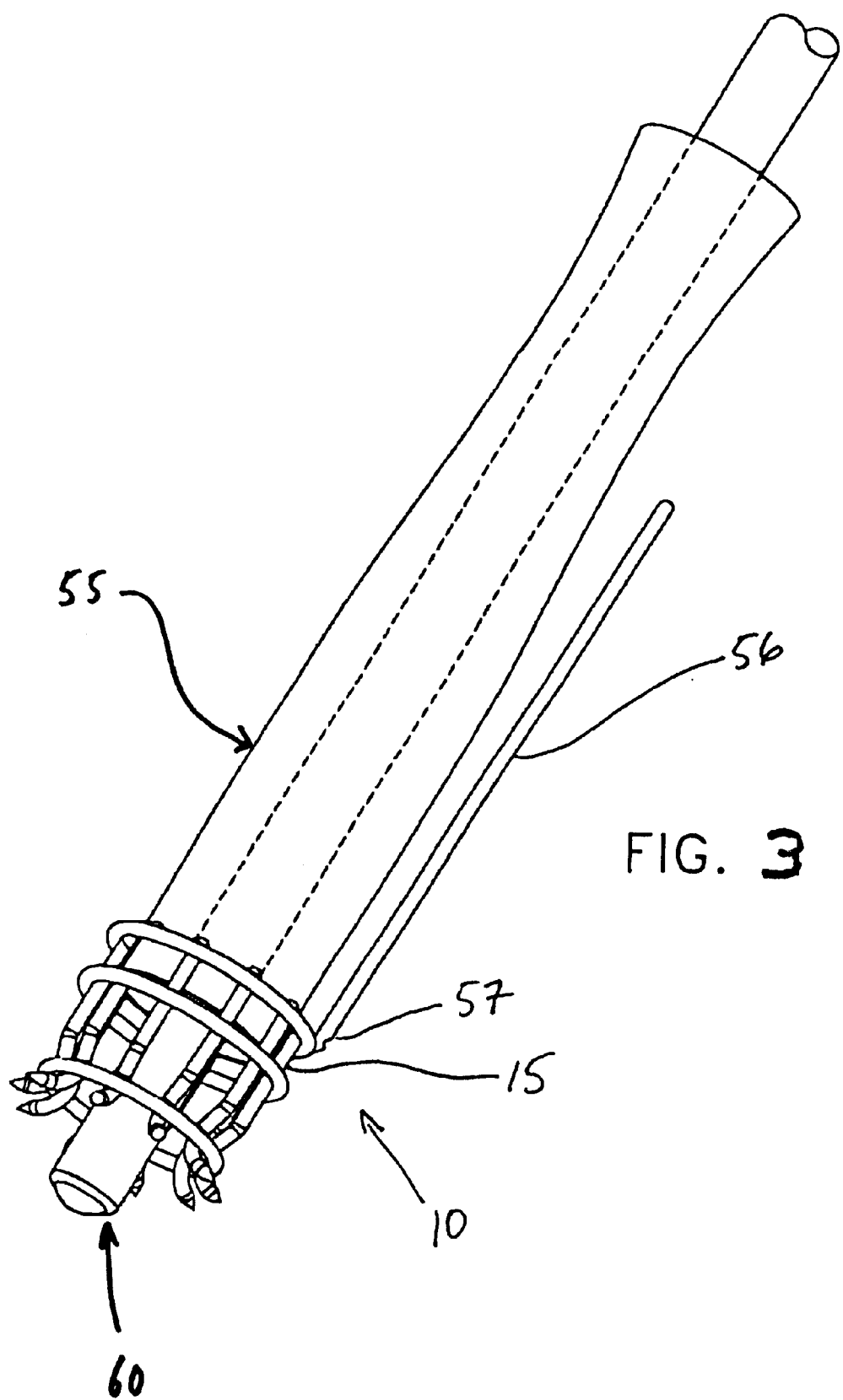
FIG. 3 illustrates a crown including a handle.

Referring to FIGS. 1–3, an apparatus 10 is shown for surgical formation of an anastomosis. In a preferred embodiment, apparatus 10 includes a crown 15 with a plurality of strands 20 joined together by at least two rings 25. Each strand 20 is joined to rings 25 adjacent a first end 30 and has a pointed barb 35 at a second end 40. Strand 20 includes a curved portion 45 adjacent barb 35 and second end 40. Curved portion 45 may be in the form of a hook.

Now looking at FIG. 2A, crown 15 is shown with a retaining ring 50 for restraining hooks 45 of each strand 20. Retaining ring 50 allows positioning of second end 40 of crown 15 adjacent tissue of physiological vessels. Removal of retaining ring 50 causes deployment of hooks 45 which secure to one, or more, physiological vessels.

Figure 4A:
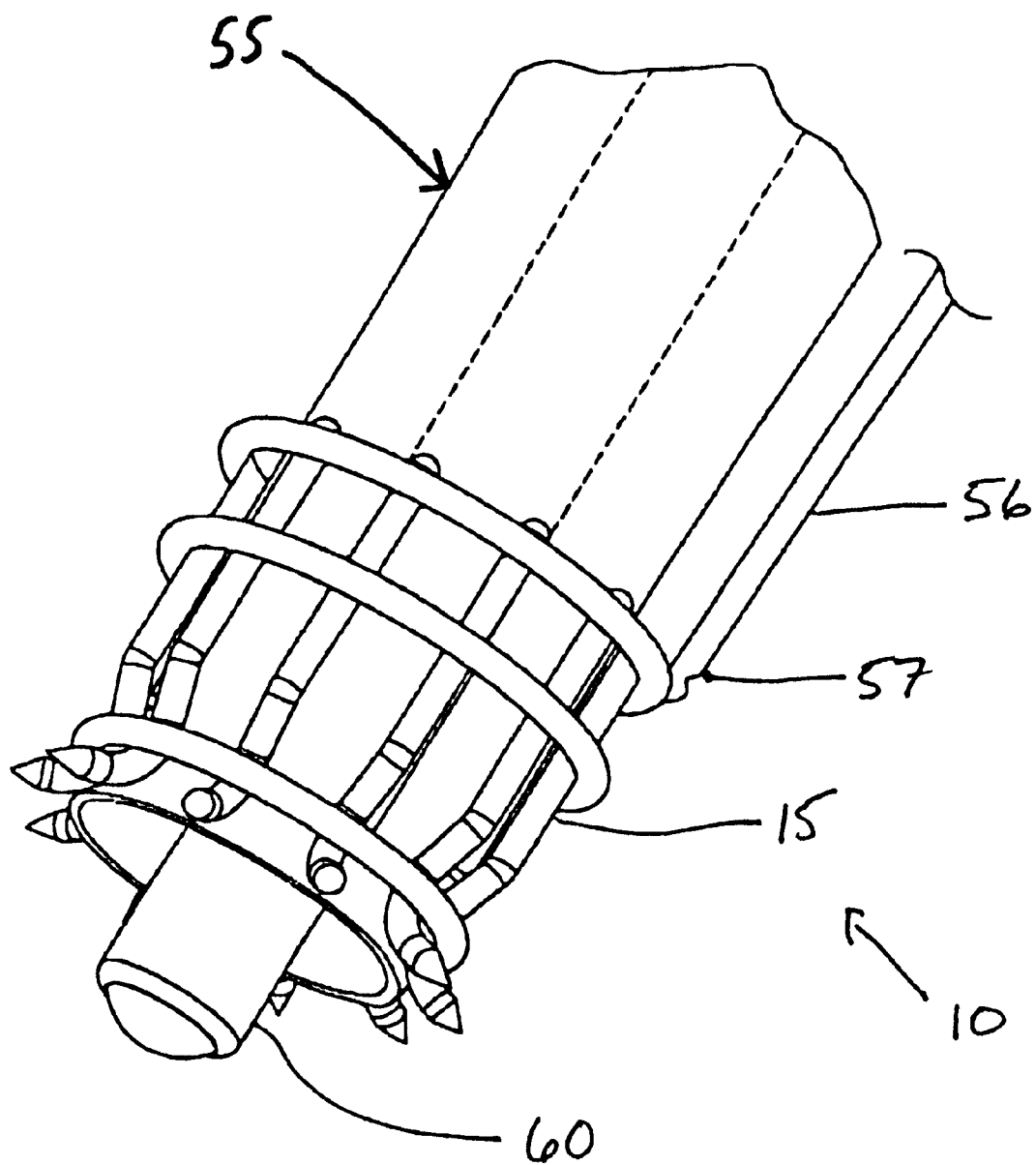
FIGS. 4A–4N illustrate various embodiments of an apparatus for surgical anastomosis using an eversion technique.
Figure 4B:
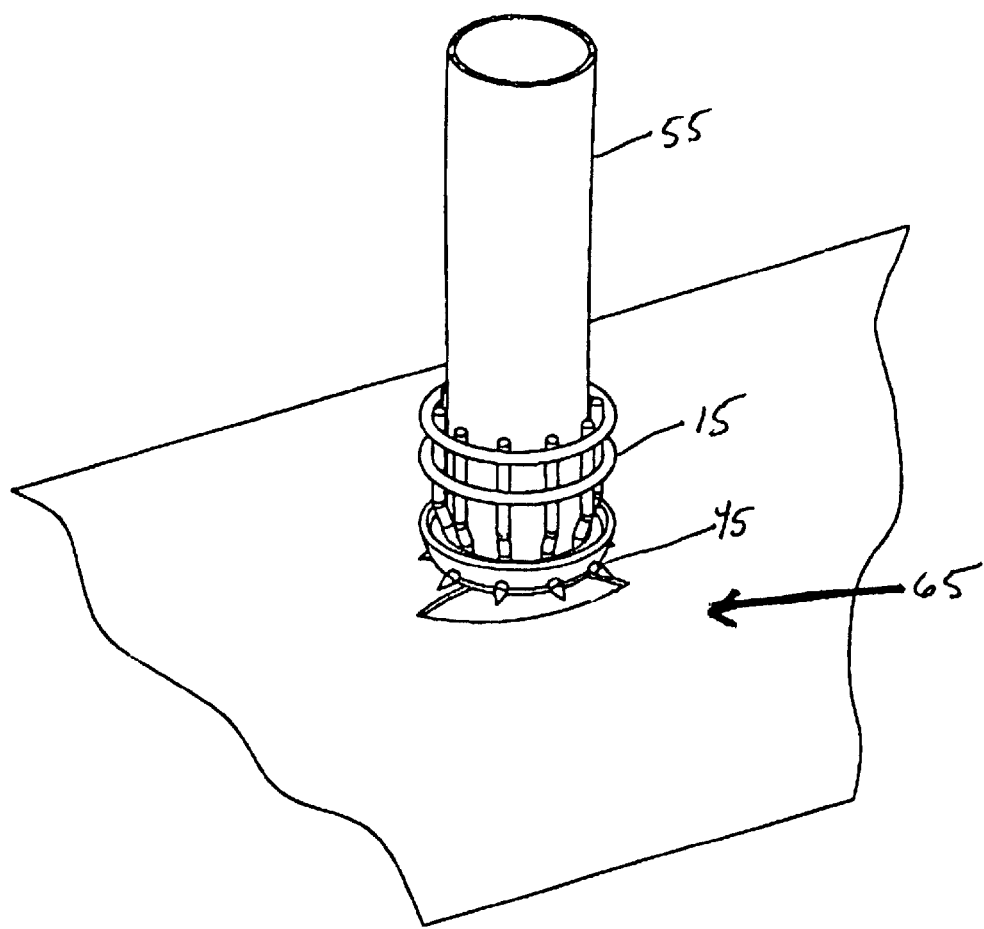
Figure 4C:
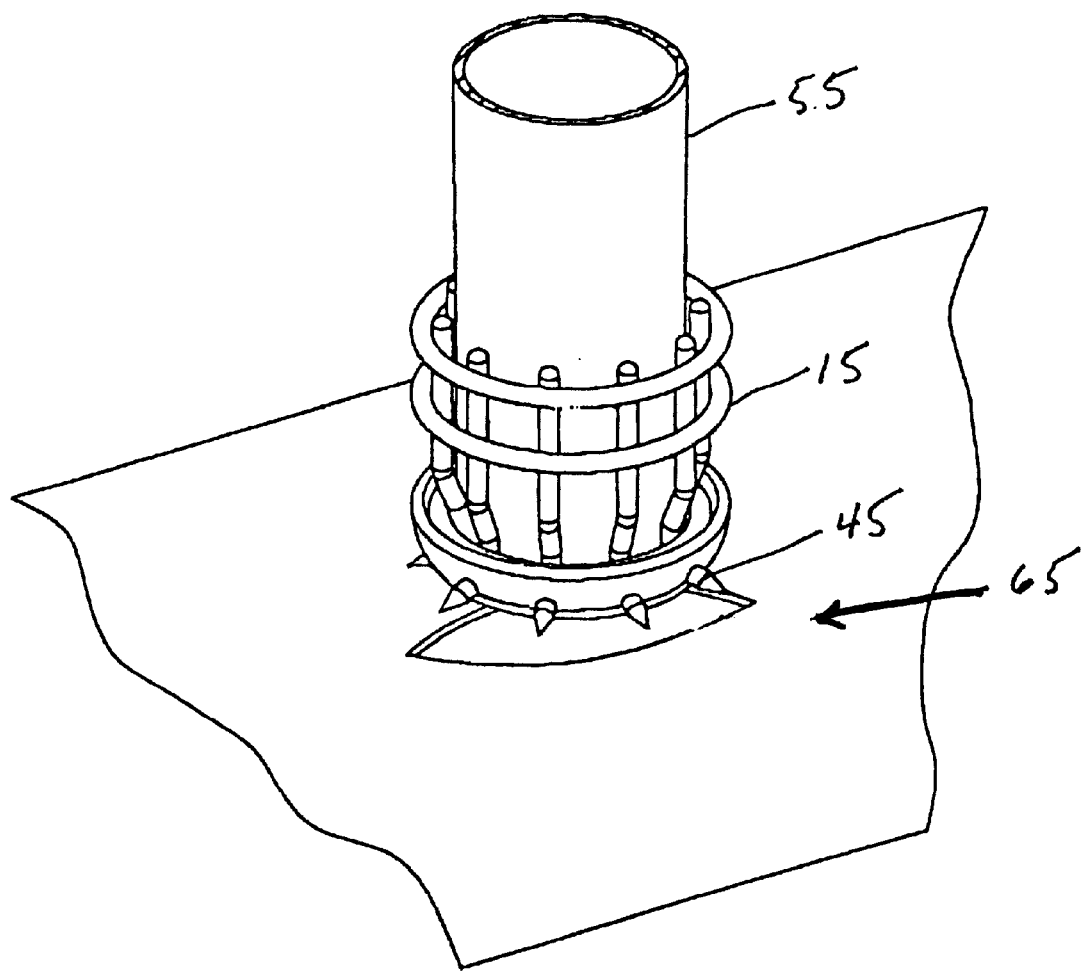
Figure 4D:
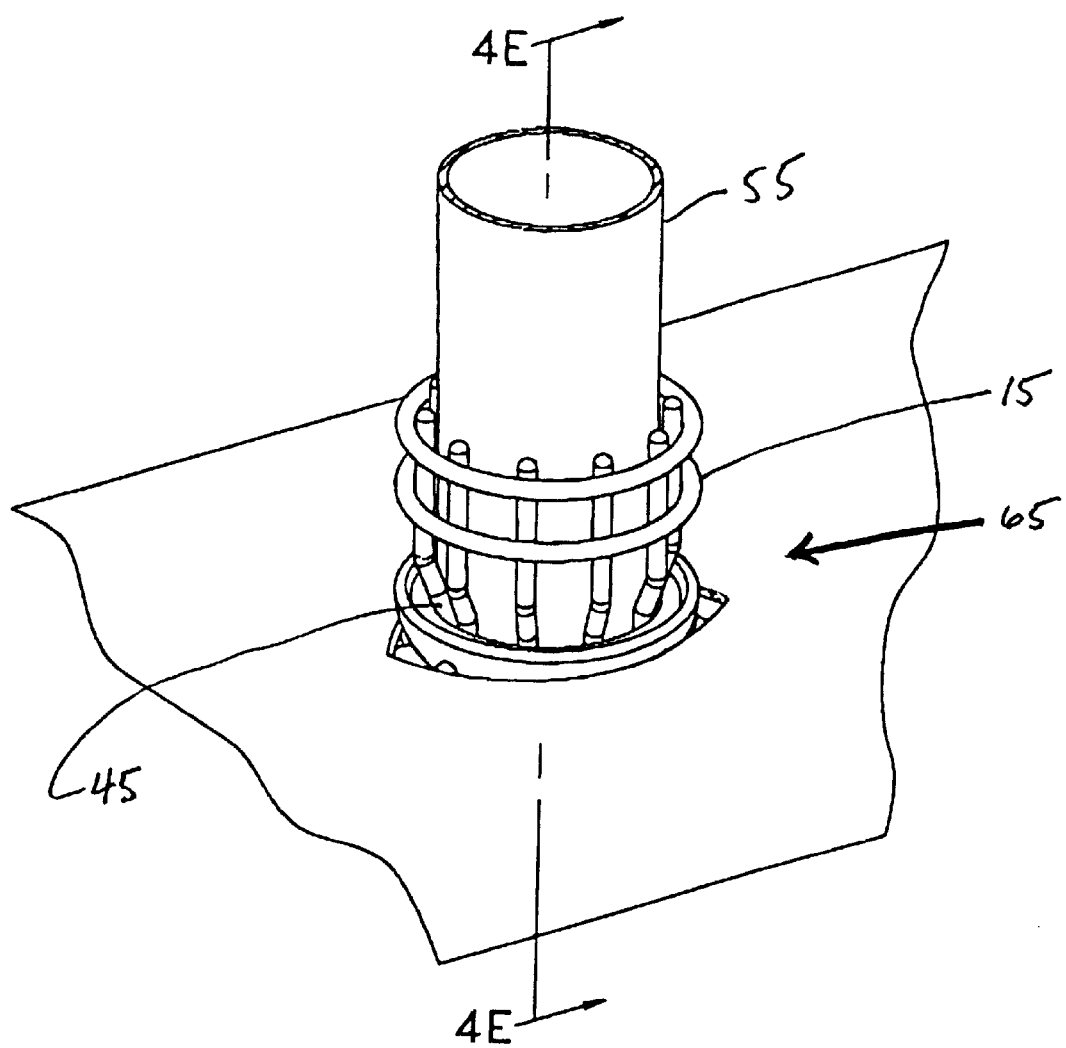
Figure 4E:
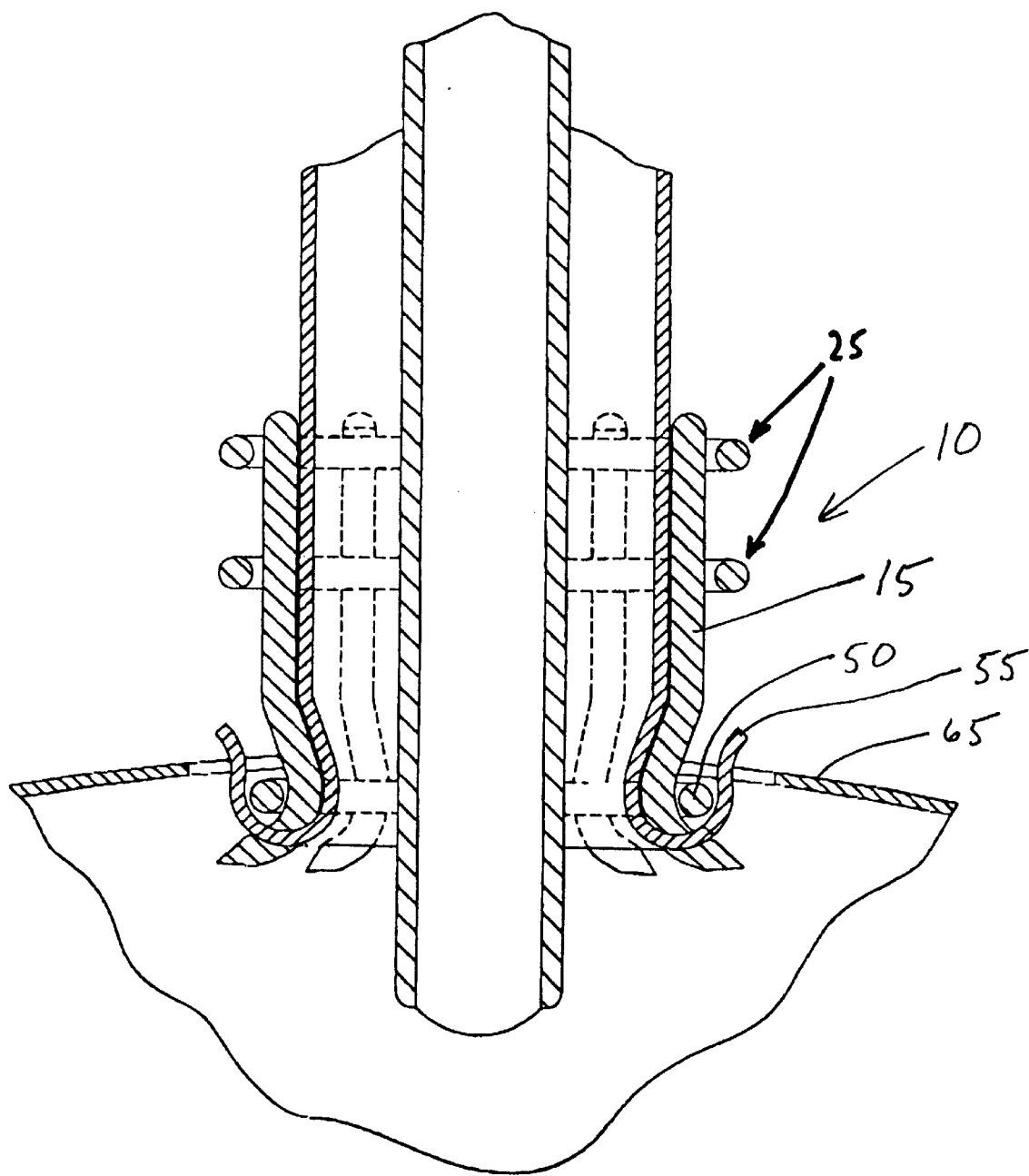
Figure 4F:
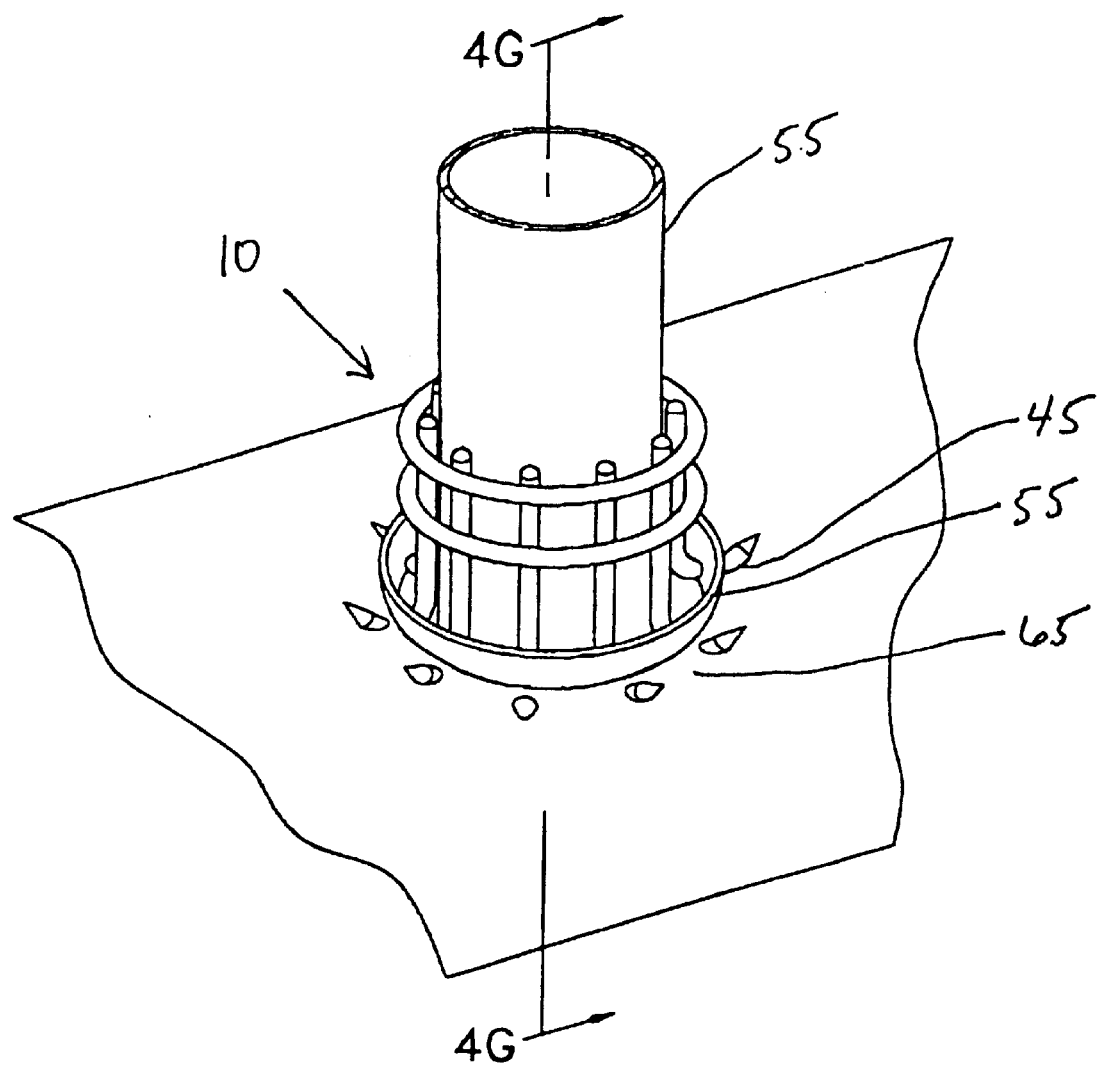
Figure 4G:
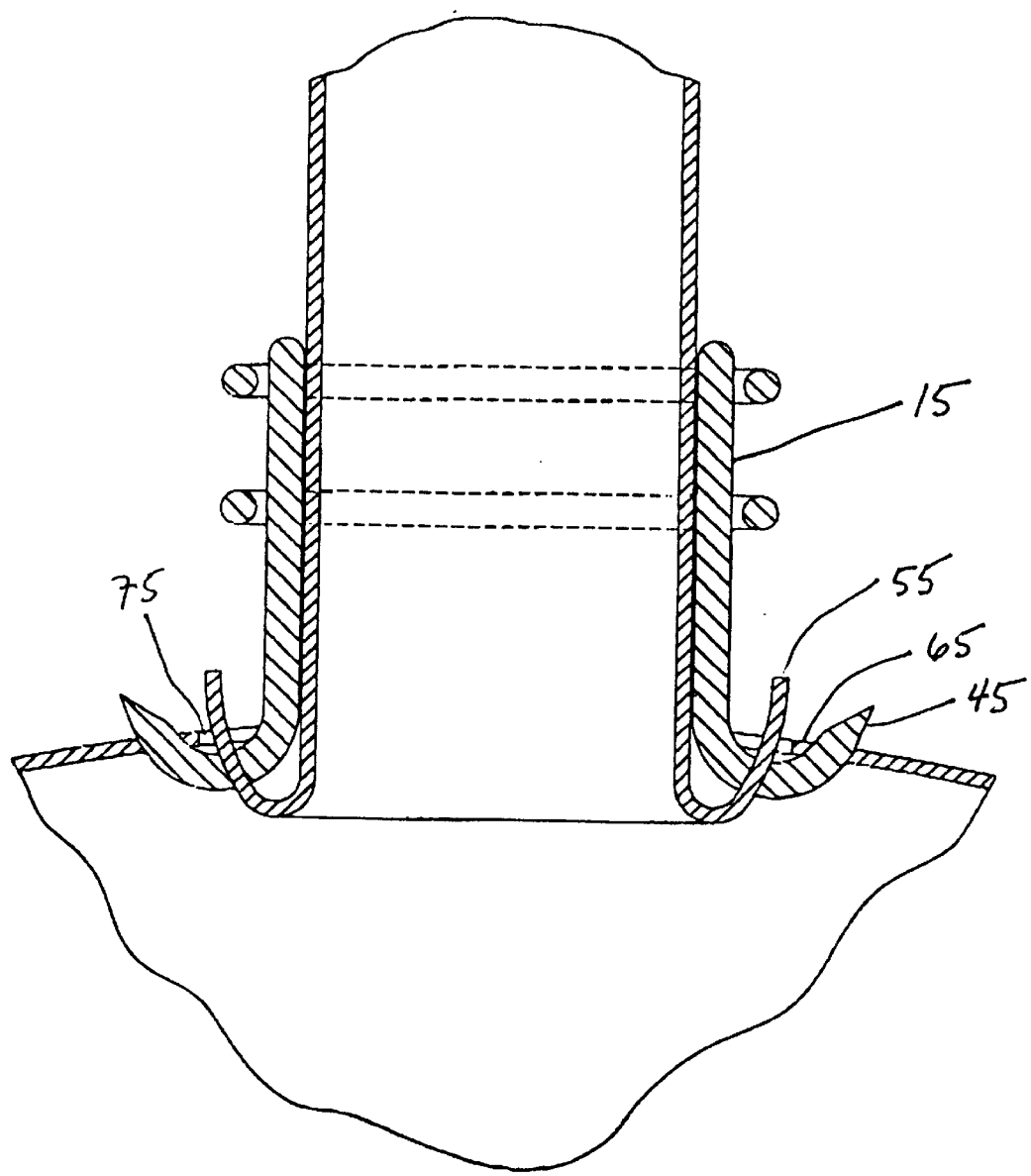
Figure 4H:
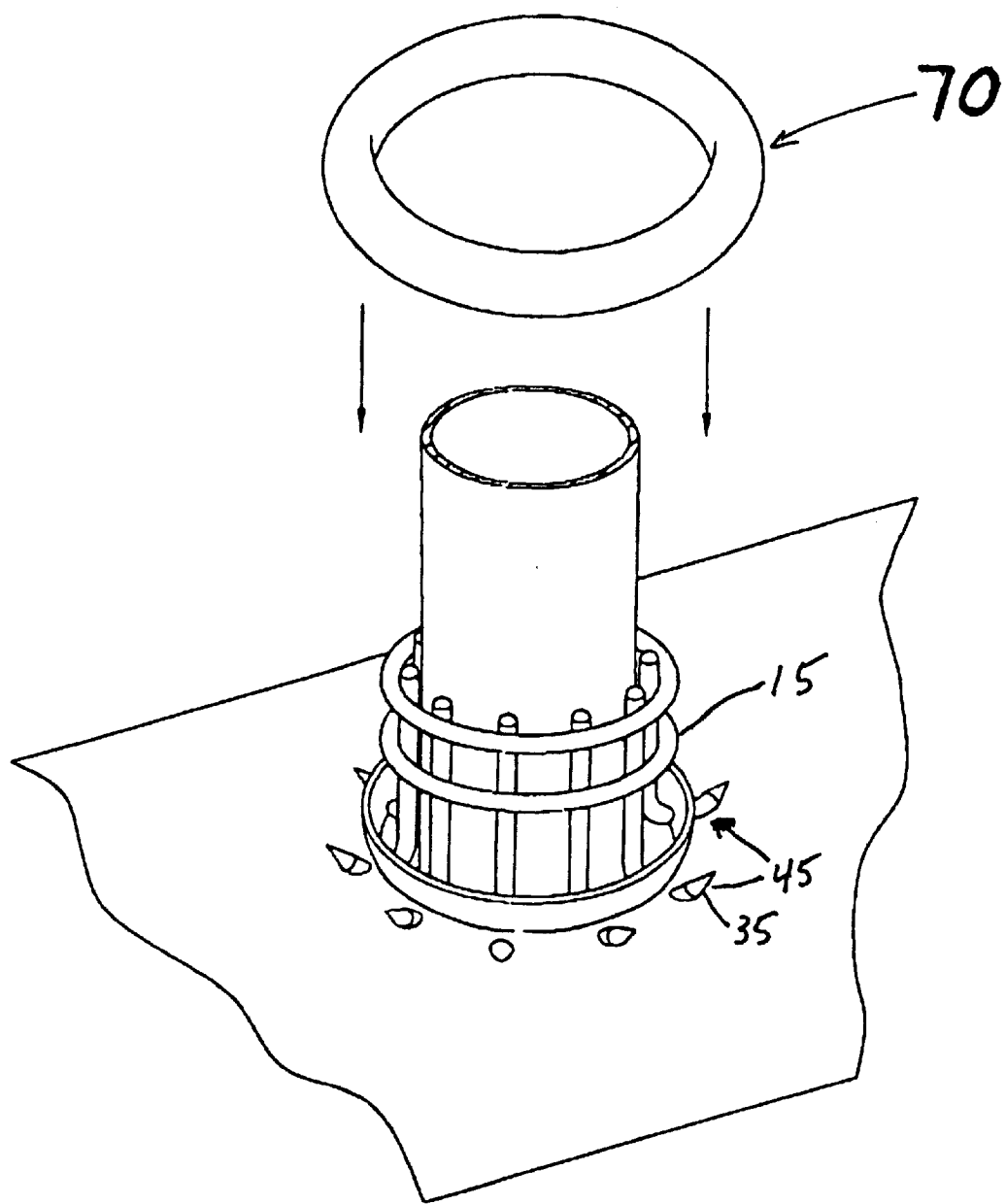
Figure 41:
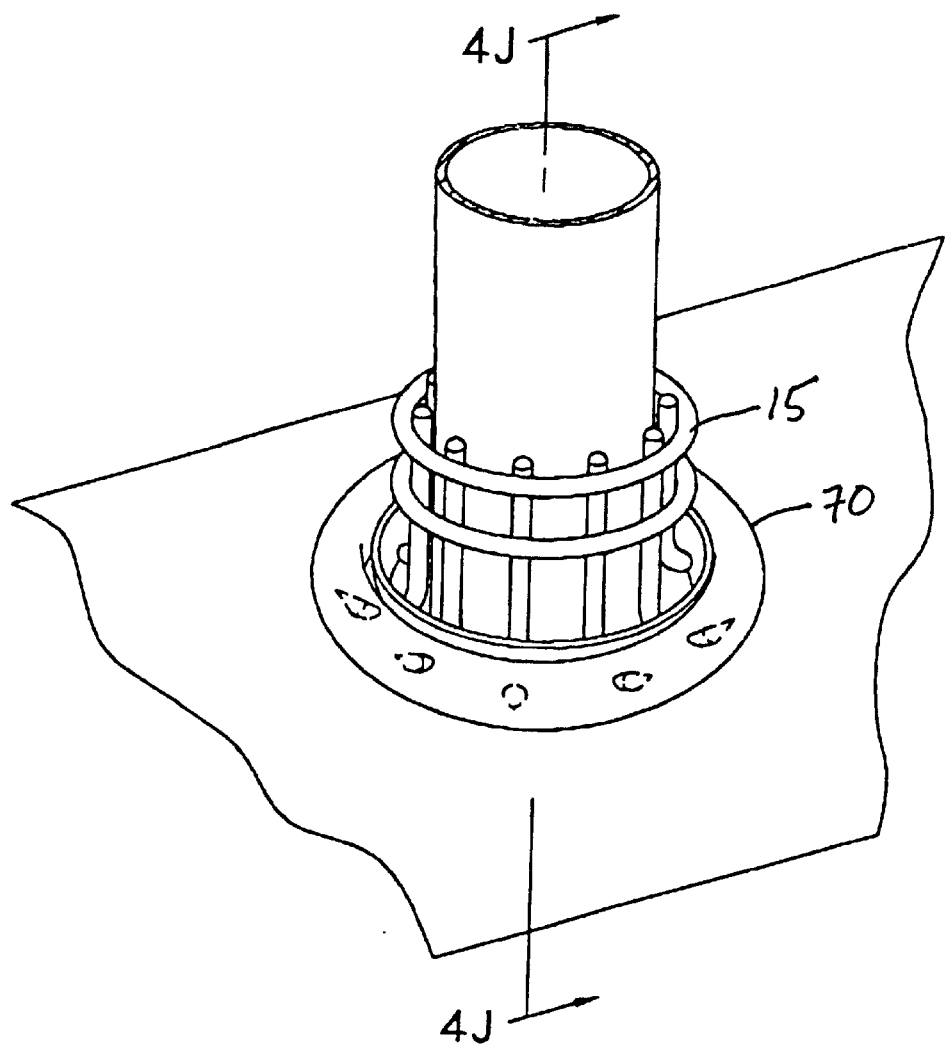
Figure 4J:
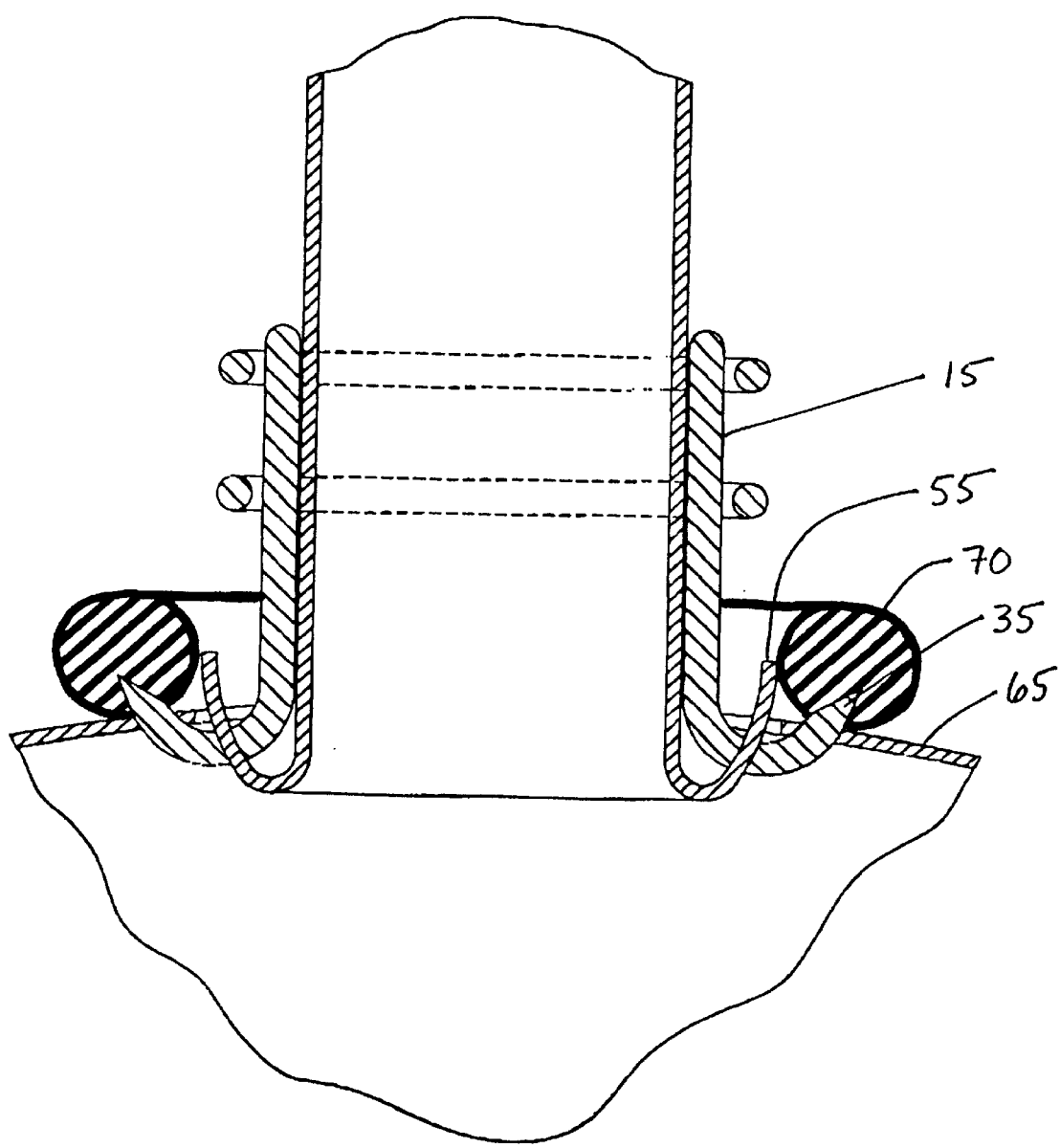
Figure 4K:
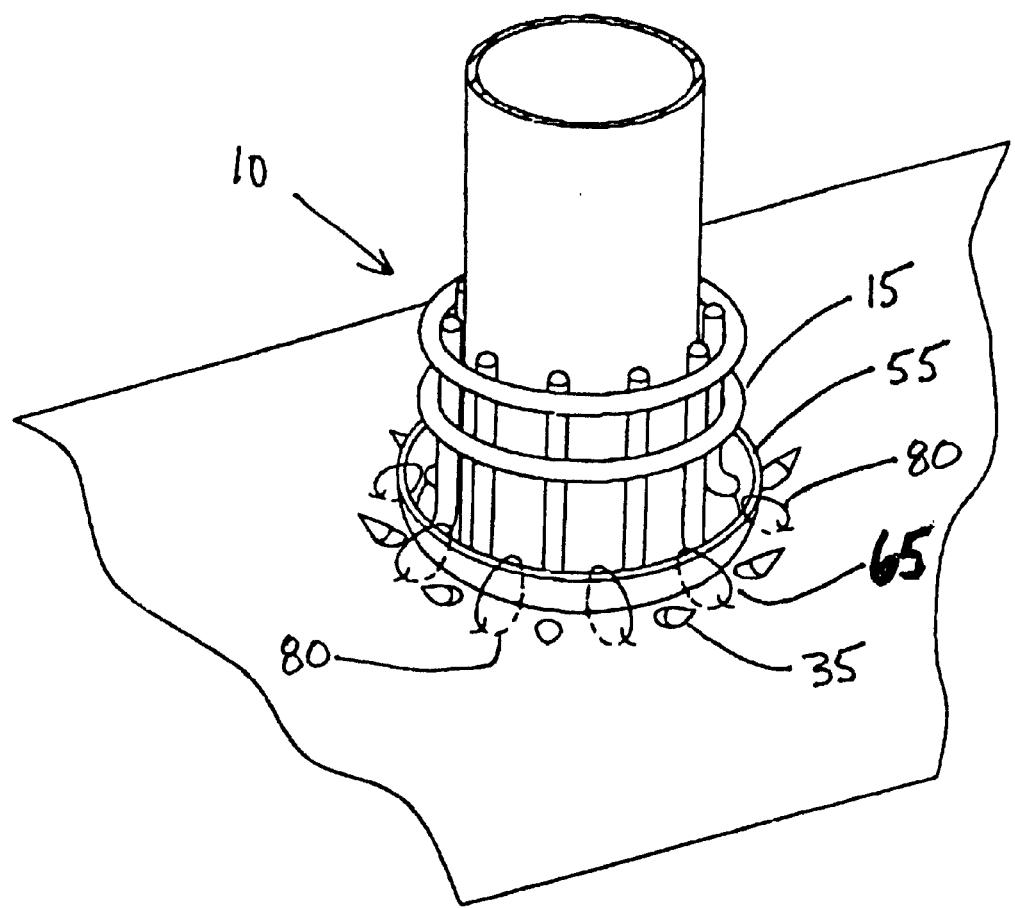
Figure 4L:
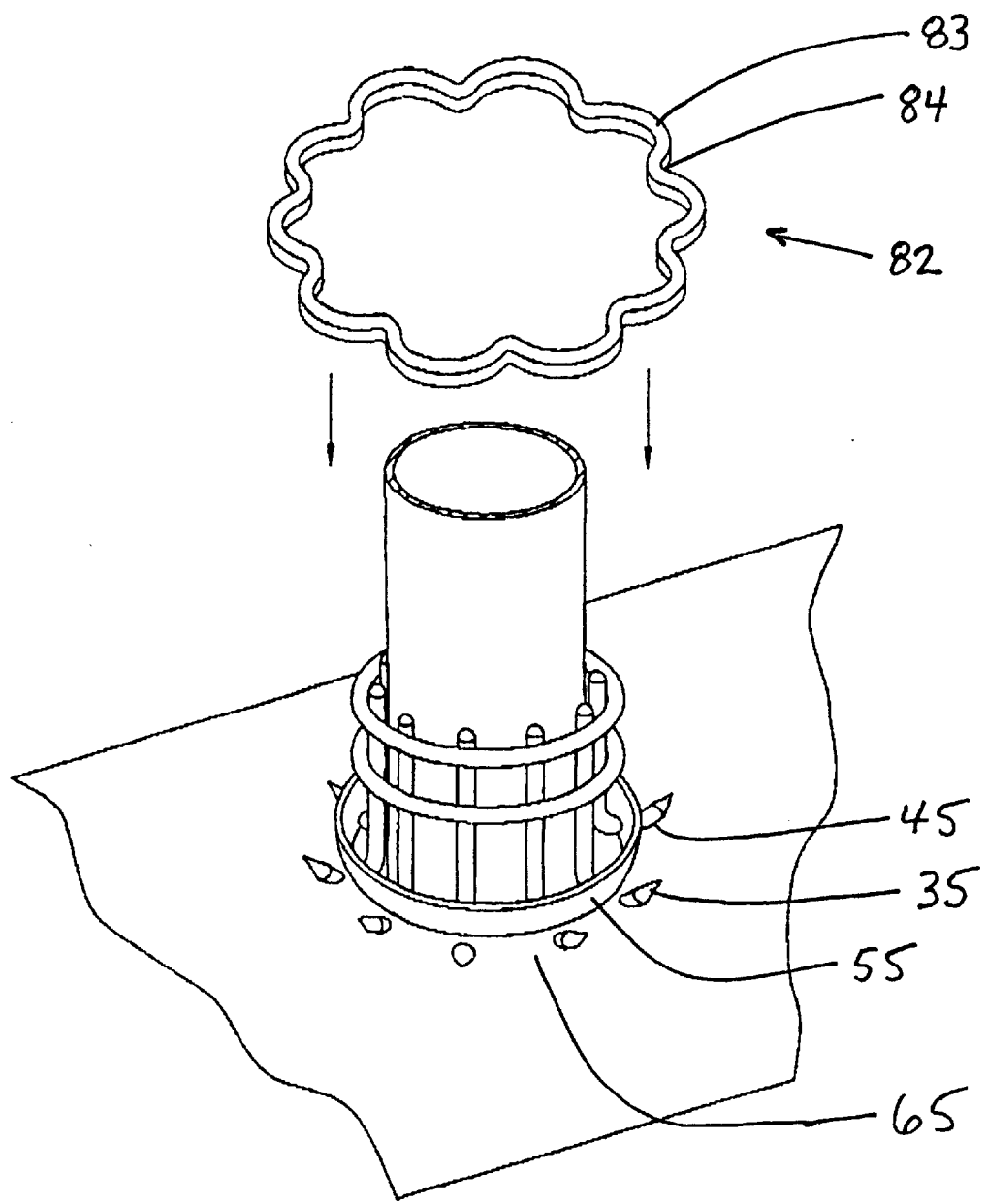
Figure 4M:
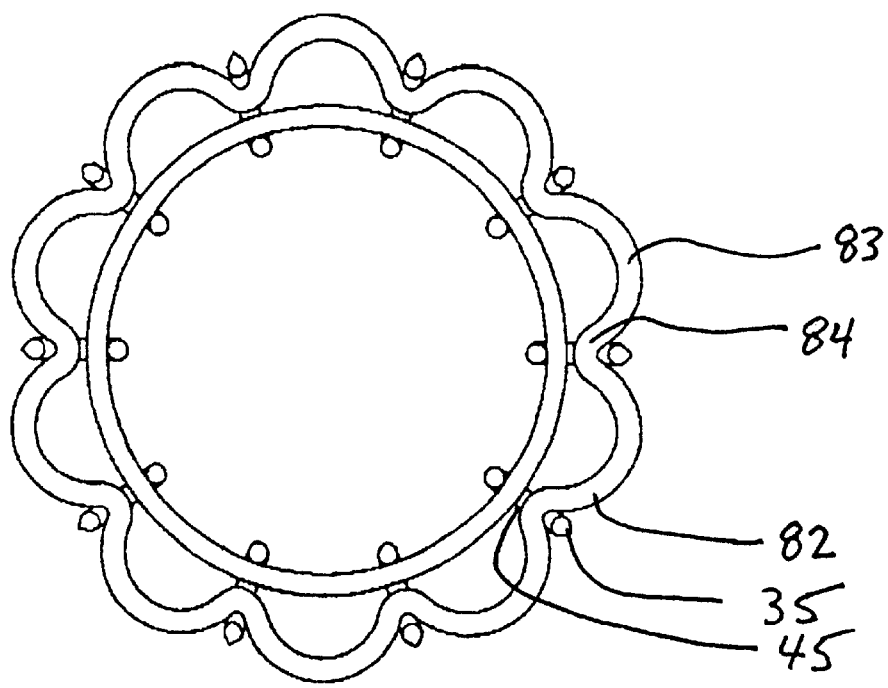
Figure 4N:
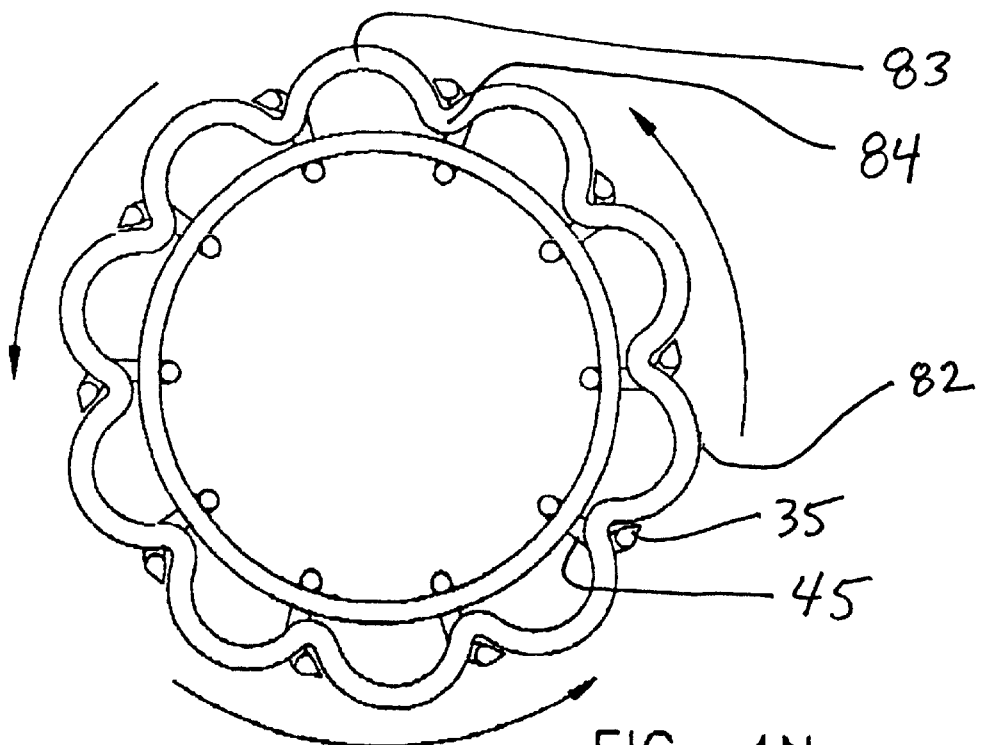

FIGS. 3 and 4A–4N illustrate a method for surgical formation of an anastomosis of vessels, referred to as an eversion technique.

In FIG. 3, apparatus 10 is positioned over one end of a physiological vessel 55 and a scope 60 positioned therethrough is shown. A handle 56 attached to crown 15 is provided to manipulate apparatus 10. Handle 56 contains a separation means 57 which includes, but is not limited to, a prefabricated breaking point.

In FIG. 4A, the progression of crown 15 up the length of vessel 55 is shown. After crown 15 is positioned a suitable distance along vessel 55, the end of vessel 55 is folded back and impaled upon hooks 45 as shown in FIG. 4B. Next, crown 15 surrounding vessel 55 is positioned within physiological vessel 65 as shown in FIG. 4D and as shown in a cross-sectional view in FIG. 4E. Retaining ring 50 is shown in the cross-sectional view of FIG. 4E and is accessible to the outside of the apparatus 10. Retaining ring 50 is removed by cutting therethrough. Alternatively, retaining ring 50 may be removed from hooks 45 by other methods such as repositioning to an area adjacent rings 25.

Now looking at FIGS. 4F and 4G, apparatus 10 is shown after retaining ring 50 is removed and hooks 45 are driven through vessel 65. As shown in FIG. 4G, a gap 75 may be created between vessel 55 and vessel 65 during the eversion technique.

In one embodiment of the invention, a sealing ring 70 is also used in conjunction with crown 15 to form apparatus 10, as illustrated in FIGS. 4H–4K. Sealing ring 70 is formed of a puncturable, implantable material such as an elastic material including, but not limited to, plastic or elastomer.

Looking again at FIG. 4G, the gap 75 between vessel 55 and vessel 65 created by the eversion technique is shown. In order to eliminate gap 75, and protect hooks 45, sealing ring 70 is placed onto crown 15 as shown in FIGS. 4H and 4I. Now looking at FIG. 4J, it can be seen that the outer surface of sealing ring 70 contacts vessel 55 and vessel 65 as sealing ring 70 is impaled onto pointed barbs 35. This simultaneous contact eliminates any passageway created by gap 75. Additionally, sealing ring 70 having an appropriately sized cross-sectional radius can also contact crown 15 above hooks 45 in addition to vessel 55 and vessel 65 to provide a more secure seal of gap 75.

Now looking at FIG. 4K, an alternative embodiment includes a plurality of sutures 80, placed around apparatus 10 to close gap 75 between vessel 55 and vessel 65. Sealing ring 70 may also be used as described above for protection of pointed barbs 35 in addition to the placement of sutures 80 for closure of gap 75.

Referring to FIGS. 4L–4N, another preferred embodiment including a clover leaf bender 82 to drive the ends of hooks 45 containing pointed barb 35 toward vessel 65 is shown. Clover leaf bender 82 is formed with a series of protrusions 83 and recesses 84. As shown in FIG. 4L, clover leaf bender 82 is placed around crown 15 after vessel 55 and vessel 65 are attached to one another. Now looking at FIG. 4M, recesses 84 contain the outwardly extending ends of hooks 45 with protrusions 83 therebetween. Next, clover leaf bender 82 is rotated, as shown in FIG. 4N, to drive the ends of hooks 45 radially and downwardly toward vessel 65. In one embodiment of the invention, clover leaf bender 82 is turned to drive the ends of hooks 45 substantially parallel to vessel 65 and is then removed from crown 15. In another embodiment, clover leaf bender 82 is turned only enough to deflect the outwardly extending ends of hooks 45 and is left in contact with hooks 45. Clover leaf bender 82 acts in a similar manner as sealing ring 70 when left in attachment to crown 15.

Figure 5A:
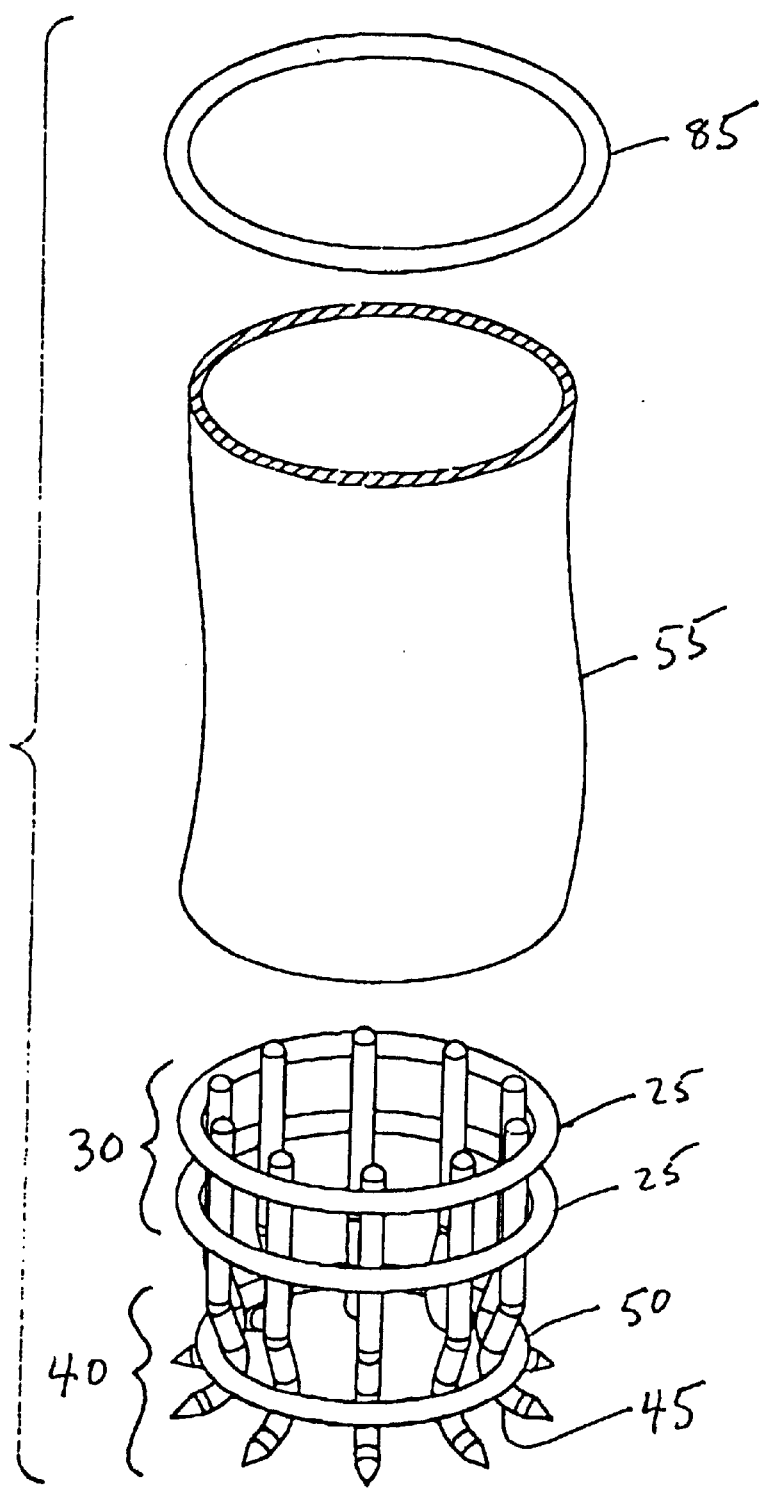
FIGS. 5A–5C illustrate an internal version of a crown.
Figure 5B:
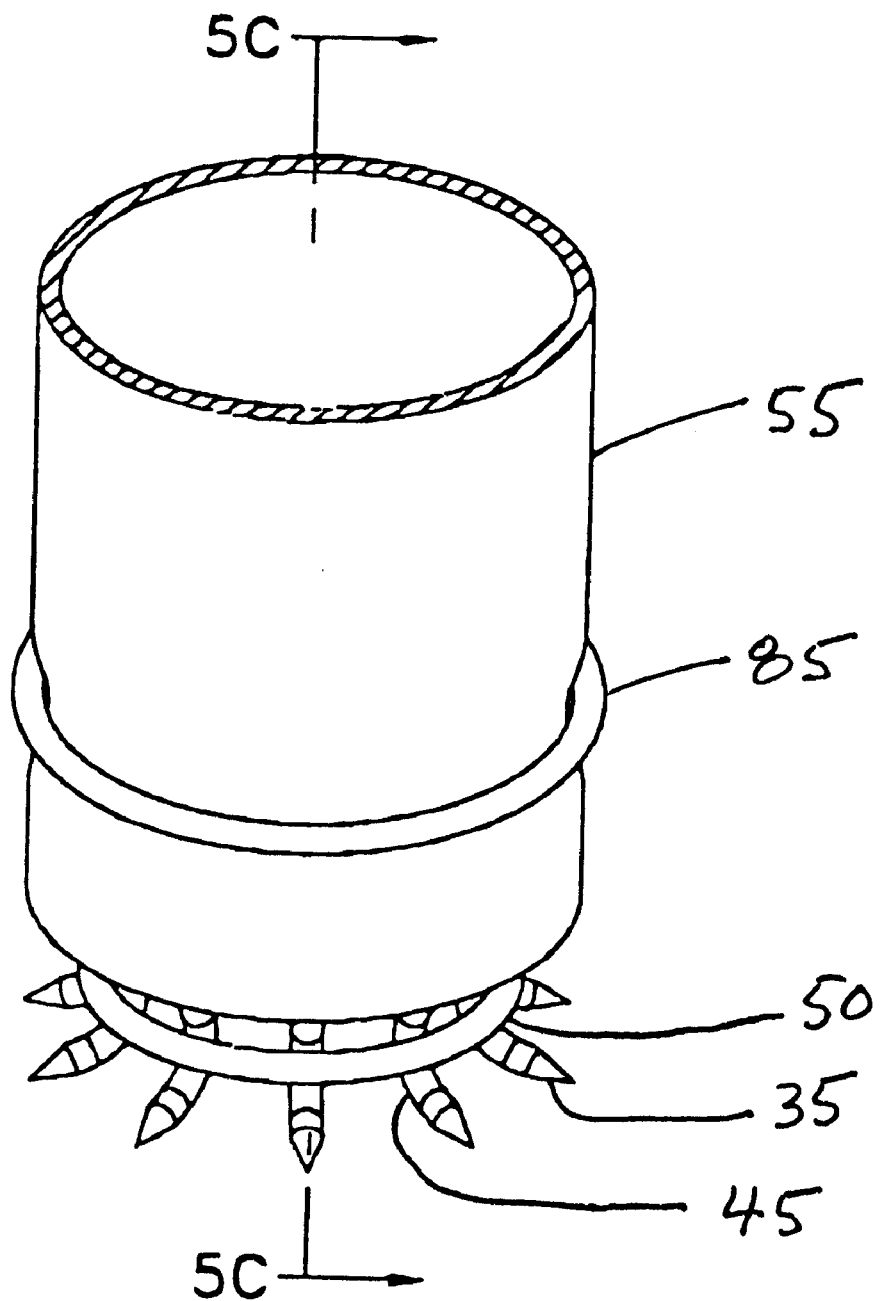
Figure 5C:
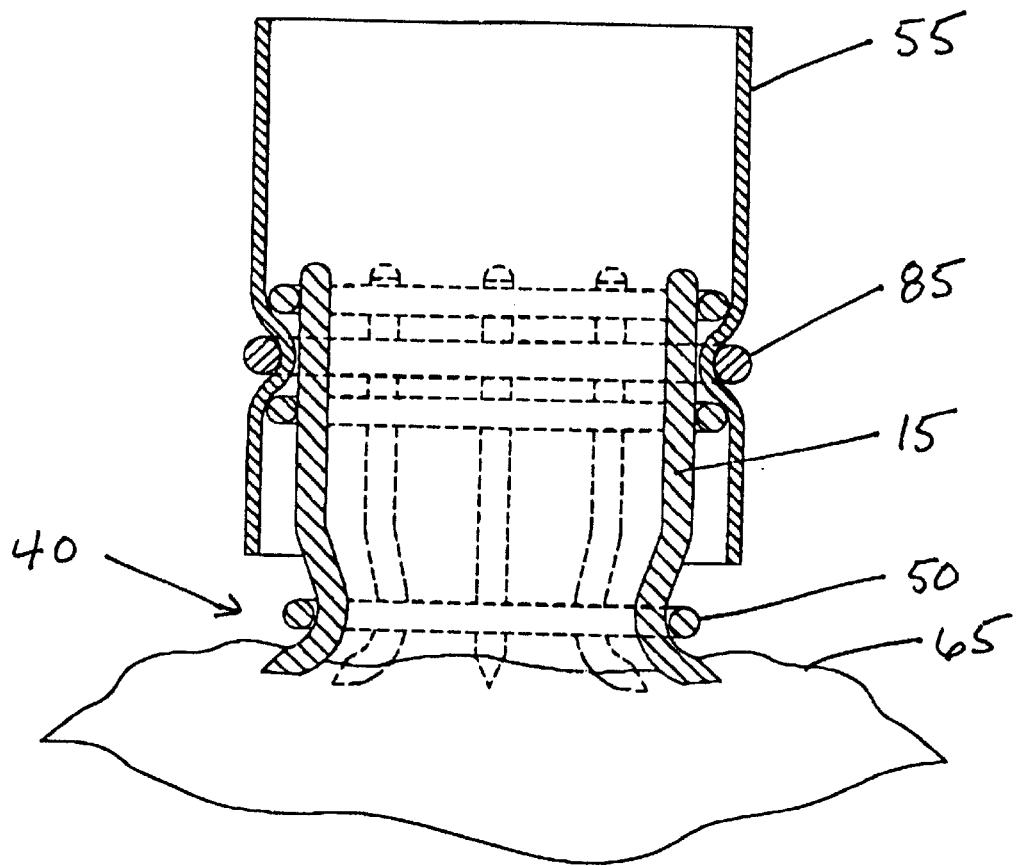

FIGS. 5A–5C illustrate an alternative arrangement in which crown 15 is placed within physiological vessel 55. As shown in FIG. 5A, lock ring 85 is provided to secure crown 15 within vessel 55 and hooks 45 are restrained by retaining ring 50 prior to insertion into vessel 65. Now looking at FIG. 5B, first end 30 (shown in FIG. 5A) of crown 15 is shown inserted into vessel 55 with lock ring 85 securely fastened over vessel 55 between crown rings 25. Hooks 45 are still restrained by retaining ring 50 for insertion of second end 40 (shown in FIG. 5A) of crown 15 into vessel 65. Referring to FIG. 5C, second end 40 of crown 15 is shown during insertion into vessel 65. Retaining ring 50 is removed, preferably by cutting, and hooks 45 deploy to secure crown 15 to vessel 65 as described above. In addition, other embodiments described herein, such as sealing ring 70 and/or sutures 80, may be implemented to further seal together vessel 55 and vessel 65.

Figure 6A:
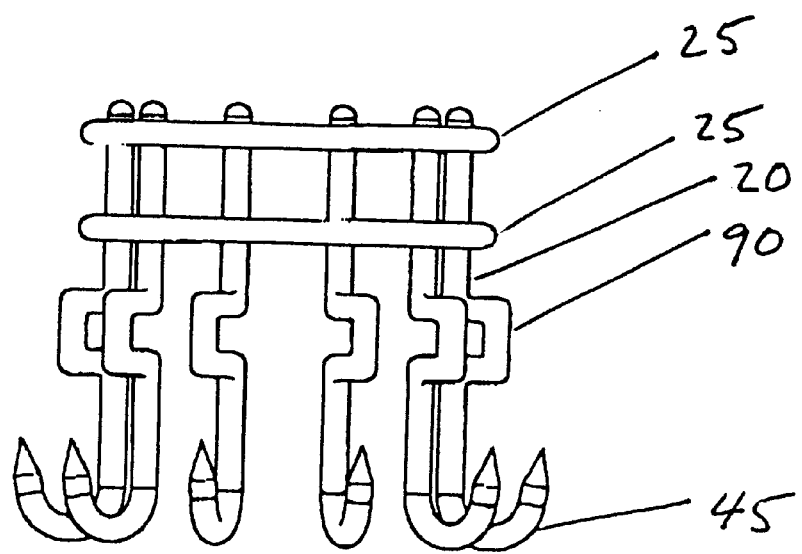
FIGS. 6A–6B, 7A–7B and 8A–8B illustrate various embodiments of strands having structures for additional flexibility.
Figure 6B:
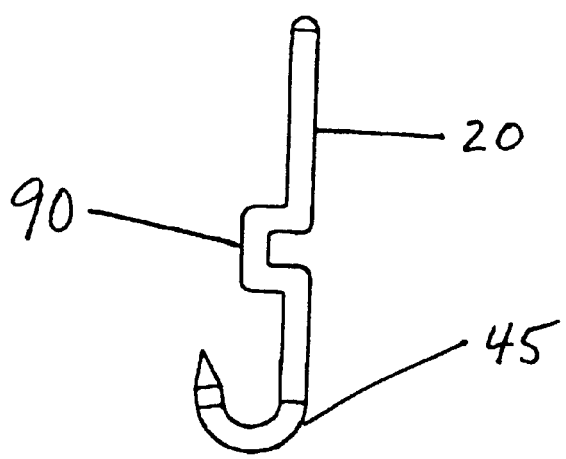
Figure 7A:
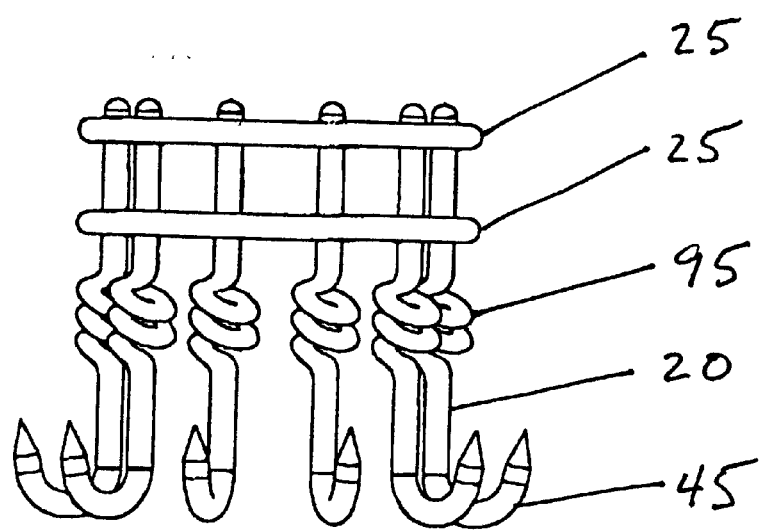
Figure 7B:
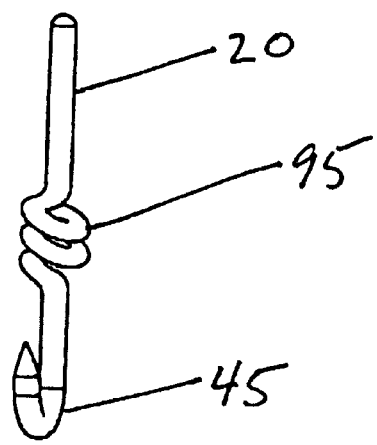
Figure 8A:
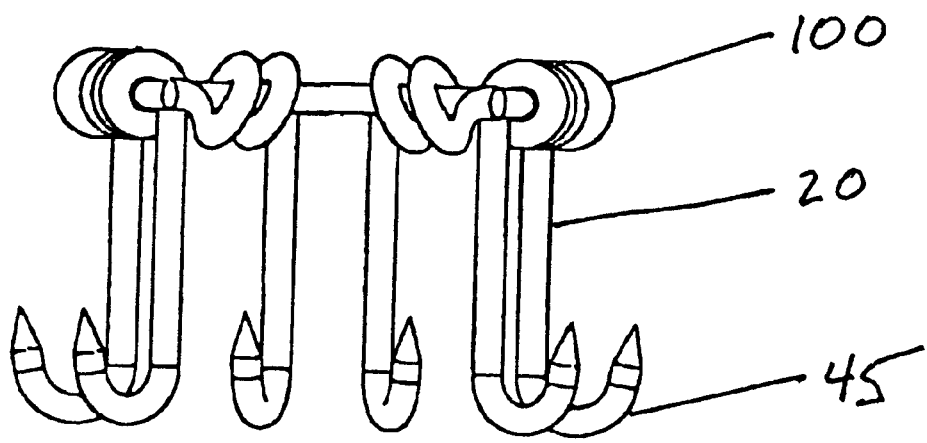
Figure 8B:
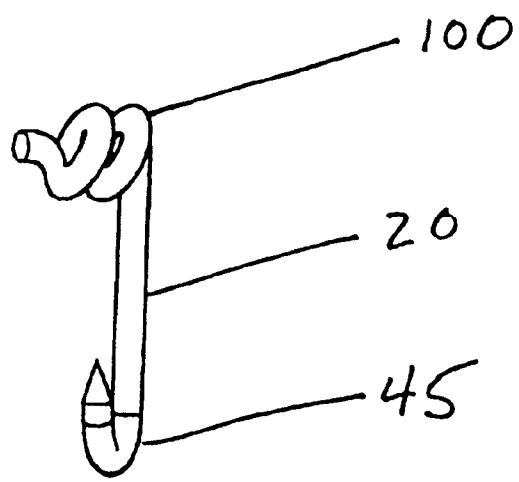

Now looking at FIGS. 6A–6B, 7A–7B and 8A–8B, alternative embodiments are shown which provide greater flexibility in strands 20 attaching hooks 45 to crown rings 25. In FIGS. 6A and 6B, an embodiment is shown in which each of the strands 20 contains a bend 90 to provide additional flexibility. In FIGS. 7A and 7B, an embodiment is shown in which each of strands 20 contains a spring 95 to provide additional flexibility. In FIGS. 8A and 8B, an embodiment is shown in which each of strands 20 uses a spring structure 100 for attachment to one of crown rings 25. Strand bend 90, strand spring 95 and spring structure 100 are advantageous in that less force is required to position hooks 45 with retaining ring 50 or with any other instrument. Strand bend 90, strand spring 95 and spring structure 100 also permit greater deflection without material failure of strand 20 and increase the force of hooks 45 to penetrate vessel 65.

Figure 9:
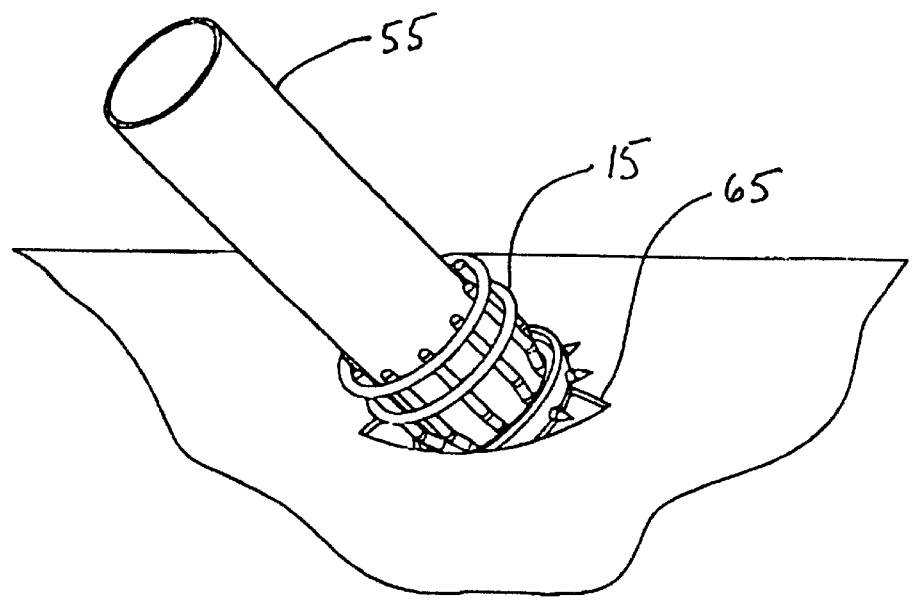
FIGS. 9–11 illustrate various eversion techniques using a crown.
Figure 10:
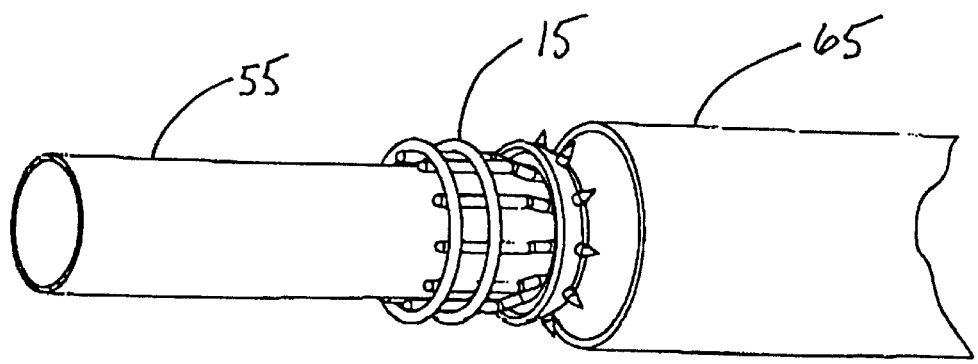
Figure 11:
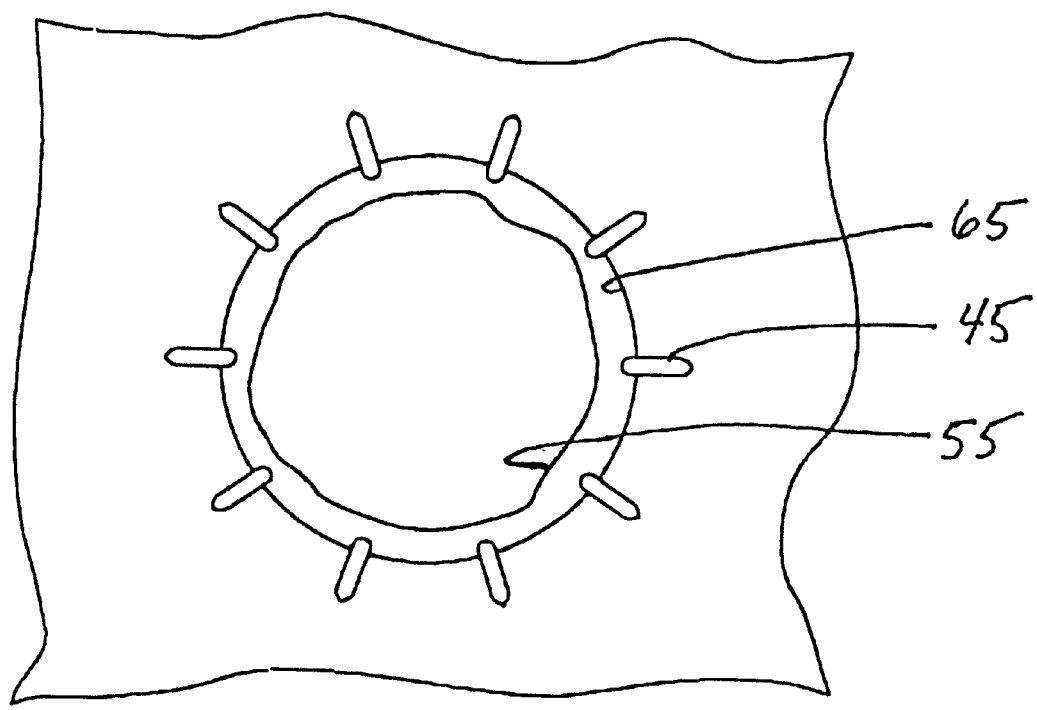

Referring now to FIG. 9, vessel 55 and vessel 65 are shown attached together using the eversion technique at an angle relative to one another. In FIG. 10, vessel 55 and vessel 65 are shown being attached together using the eversion technique in series with each other. In FIG. 11, a view is shown looking from the inside of vessel 65 attached to vessel 55 with hooks 45 about the perimeter of the attachment.

Figure 12A:
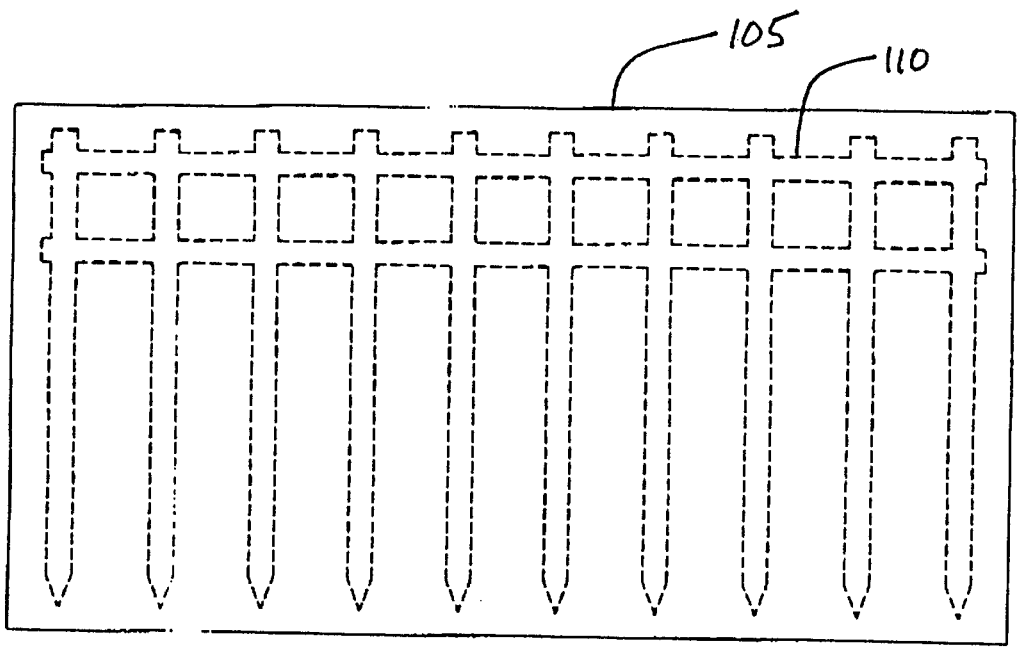
FIGS. 12A–12D illustrate a crown formed of a planar material.
Figure 12B:
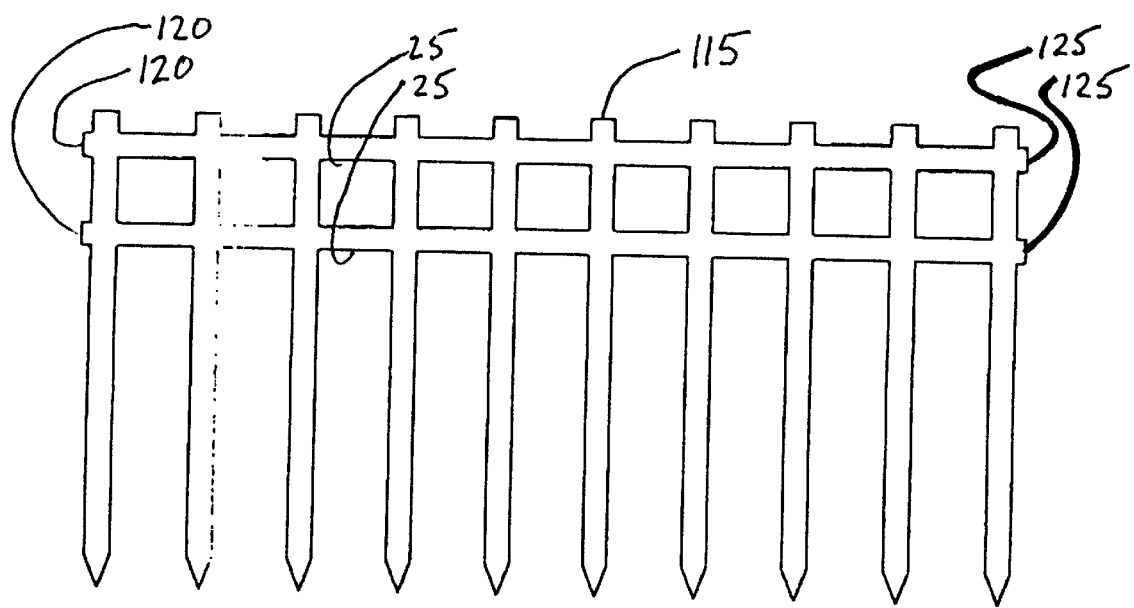
Figure 12C:
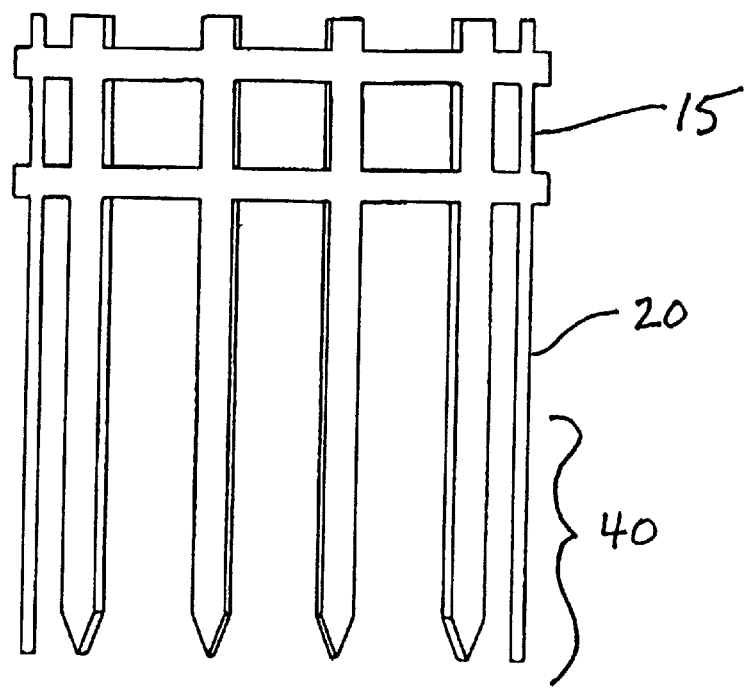
Figure 12D:
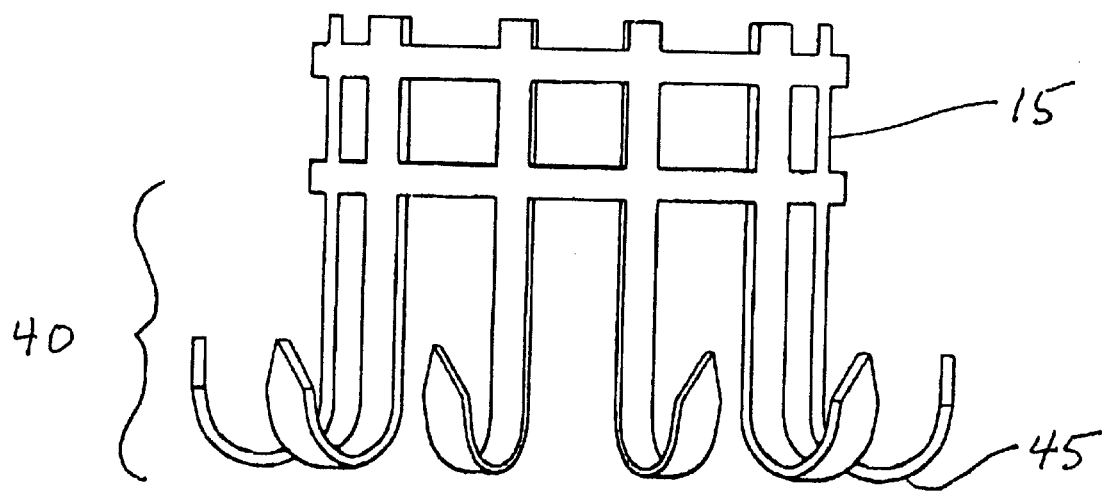

Referring to FIGS. 12A–12D, an alternative embodiment of an apparatus and method where crown 15 is stamped or etched from a sheet of material 105 is shown. In FIG. 12A, sheet 105 is shown intact before stamping or etching to create crown 15. Phantom lines 110 on sheet 105 depict the configuration of the stamping or etching. Next, crown 15 is stamped or etched from sheet 105 to form a planar crown 115 as shown in FIG. 12B. Planar crown has a first end 120 and a second end 125 on opposing ends of crown rings 25 to connect together strands 20. Planar crown 115 is rolled to connect first end 120 to second end 125 to form crown 15, as shown in FIG. 12C. Crown 15 formed by planar crown 115 has substantially straight strands 20. Then hooks 45 are formed as shown in FIG. 12D. In this configuration, crown 15 is utilized as otherwise described herein.

Figure 13A:
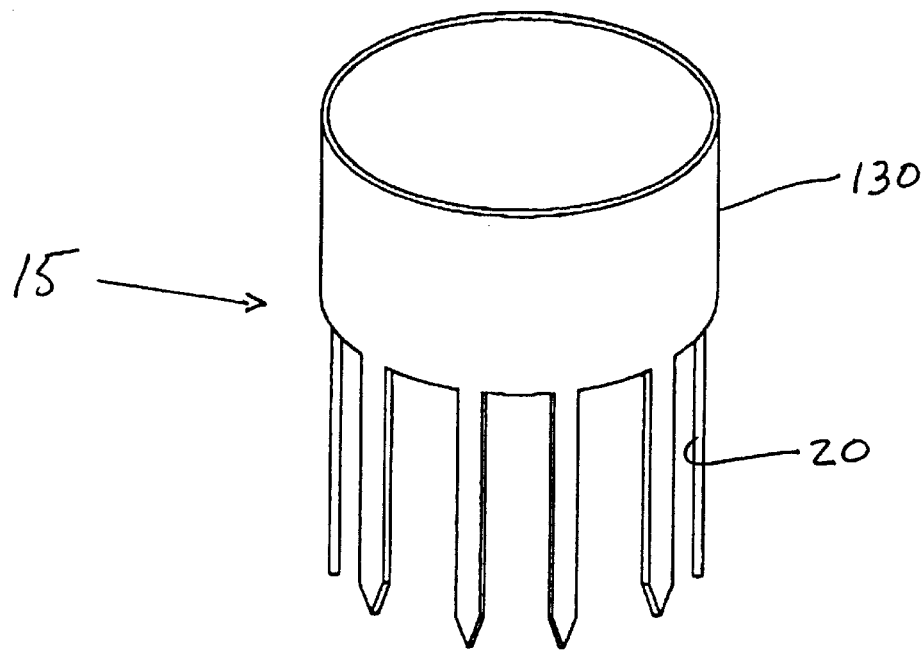
FIGS. 13A–13B illustrate a crown having a unitary ring structure.
Figure 13B:
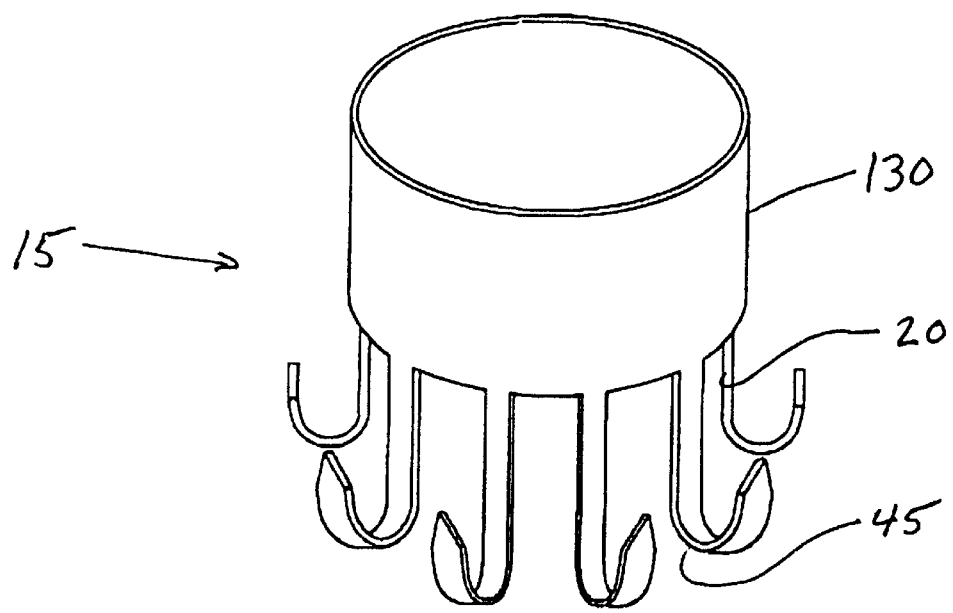

Now looking at FIGS. 13A and 13B, an alternative embodiment is shown in which crown rings 25 of crown 15 are a unitary structure 130. Crown 15 having unitary structure 130 is formed either by one of the techniques described above, by molding a single element or by using other known processes. Then hooks 45 are formed as shown in FIG. 13B. Crown 15 is attached to at least one vessel structure using the techniques described herein.

Figure 14A:
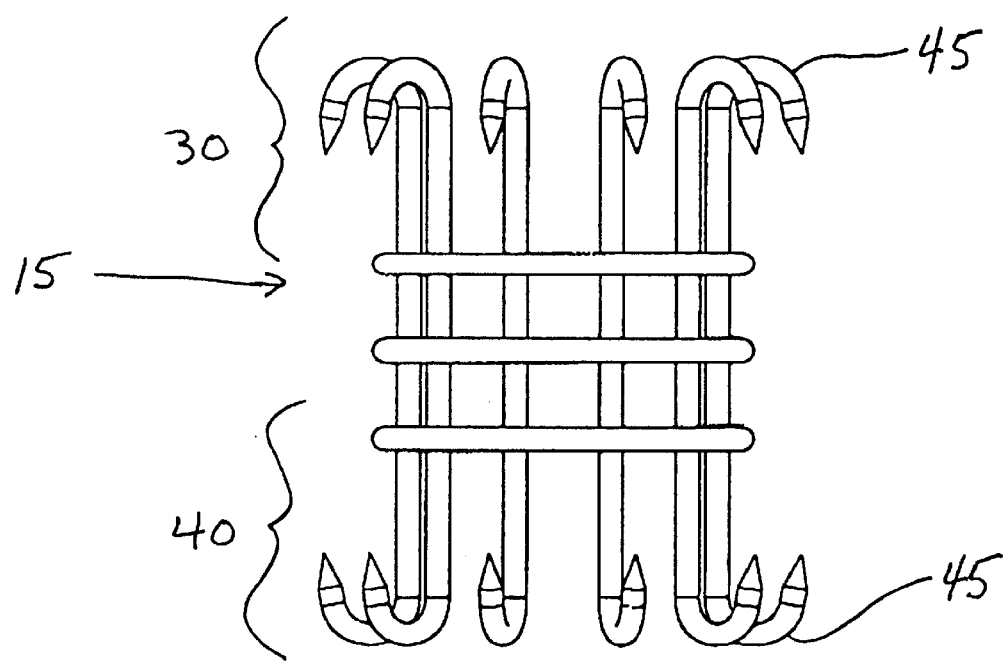
FIGS. 14A–14B illustrate an embodiment of the invention with hooks at both ends of a crown.
Figure 14B:
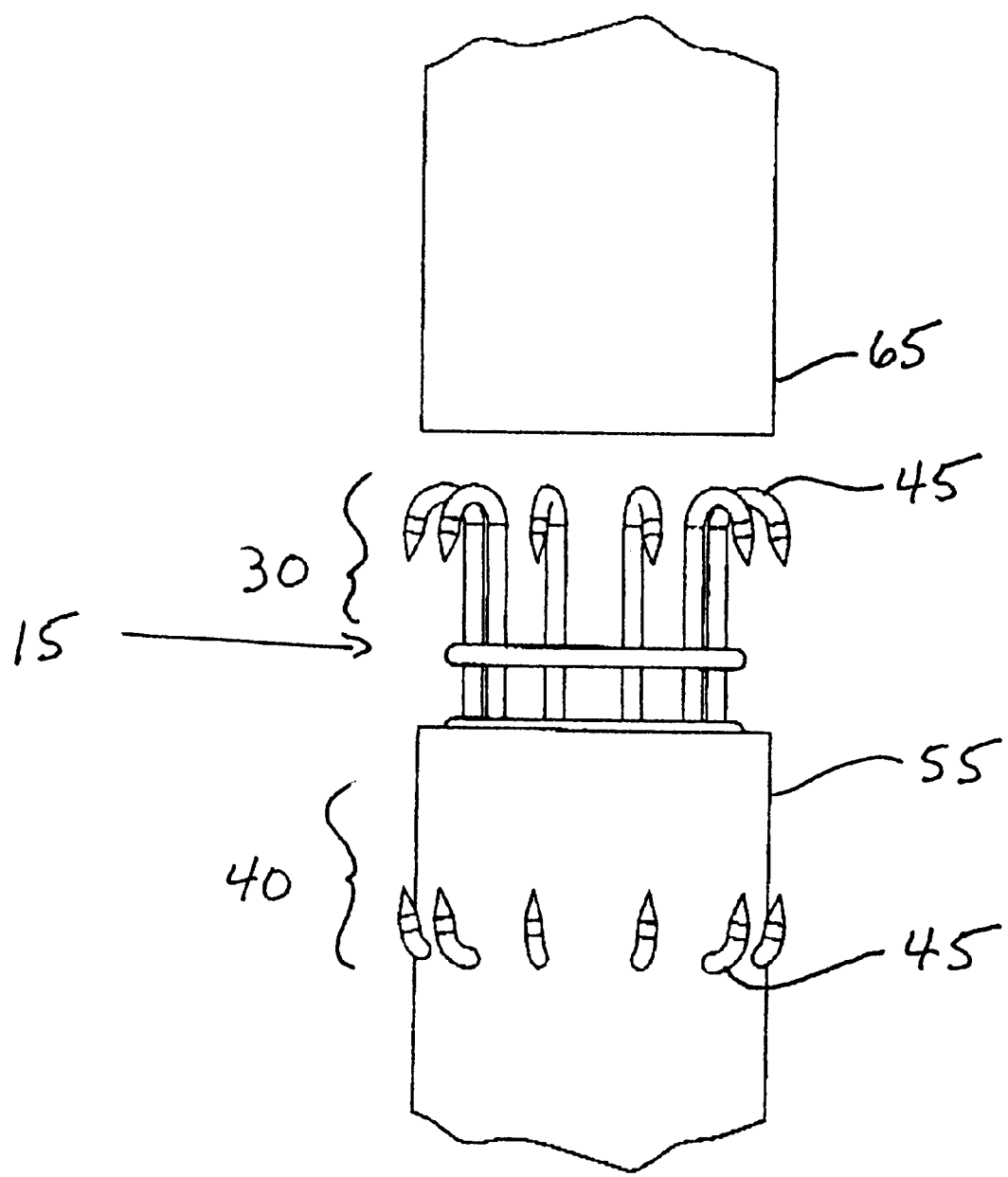

Referring to FIGS. 14A and 14B, an alternative embodiment of crown 15 having hooks 45 at both first end 30 and at second end 40 is shown. As shown in FIG. 14B, vessel 55 is attached to hooks 45 at first end 30 and then vessel 65 is attached to hooks 45 at second end 40 to complete the surgical anastomosis of the vessels. Additionally, other embodiments and methods described herein may be incorporated into this embodiment.

Figure 15B:
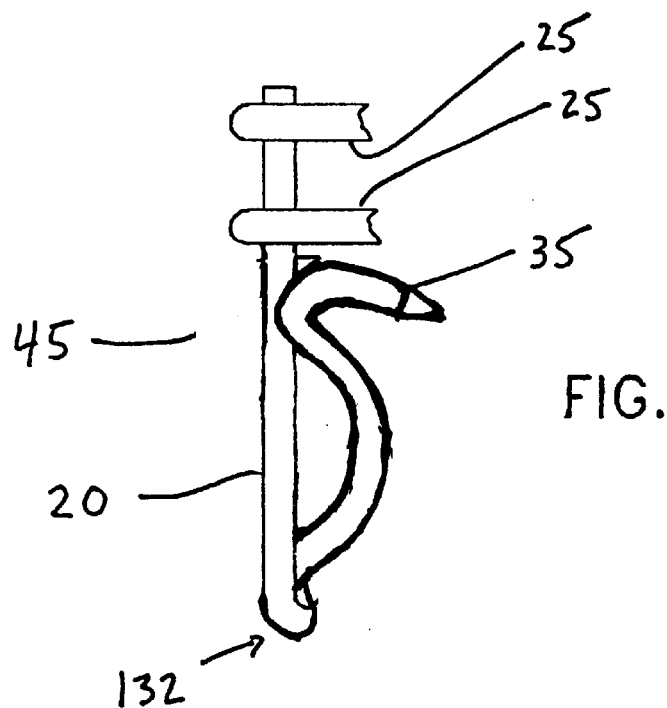
FIGS. 15A–15B illustrate an embodiment of the invention with a self-locking hook.
Figure 15A:
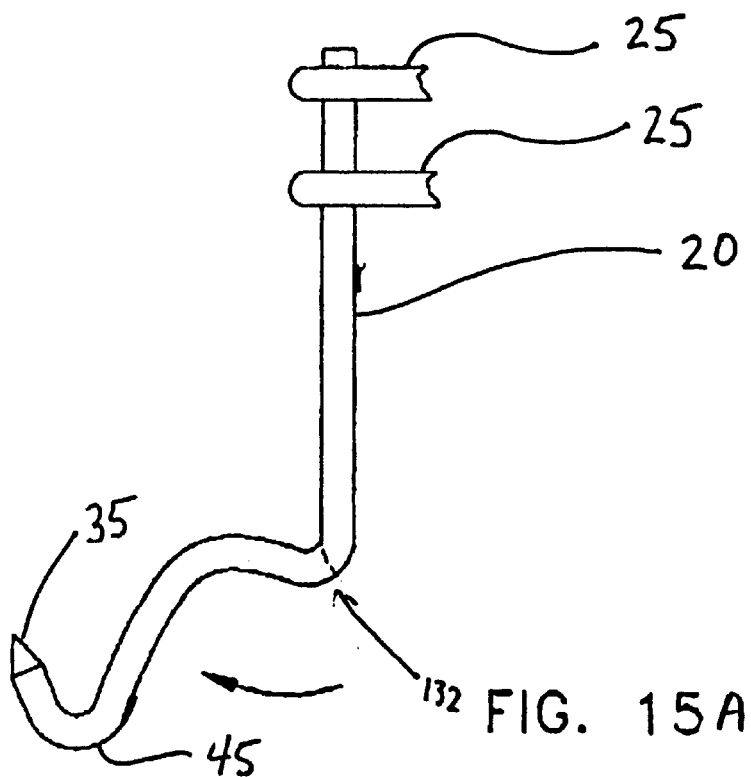

Now referring to FIGS. 15A and 15B, an alternative embodiment to restrain hooks 45 containing pointed barbs 35 is shown. Strands 20 each contain an articulating portion 132 which allows the positioning of hook 45 around and the positioning of barb 35 behind strand 20 toward first end 30 of crown 15. To deploy hook 45, second end 40 of crown 15 is positioned within a vessel. Next, hook 45 springs outward, penetrating vessel 65, and then it is snapped back around strand 20, as shown in FIG. 15B, thus capturing vessels 55 and 65.

Pointed barbs 35 include a range of structures including, but not limited to, several embodiments shown in FIGS. 16–19. In FIG. 16, pointed barb 35 is conically shaped at the end of a cylindrical shaped strand 20. In FIG. 17, pointed barb 35 is formed from a cut at an acute angle from a cylindrical shaped strand 20. In FIG. 18, pointed barb 35 is formed from a pair of cuts at acute angles at the end of a rectangular shaped strand 20. In FIG. 19, pointed barb 35 is formed in a pyramidal shape at the end of a rectangular shaped strand 20.

The preferred embodiment of the invention also includes sealants to facilitate closure of gap 75, or any other opening. Sealants are contained on crown 15 adjacent hooks 45. Sealants include, but are not limited to, various glues and clotting agents. After placement of crown 15 and effecting the surgical anastomosis, these sealants further aid in closure of any gaps and openings.

Figure 20:
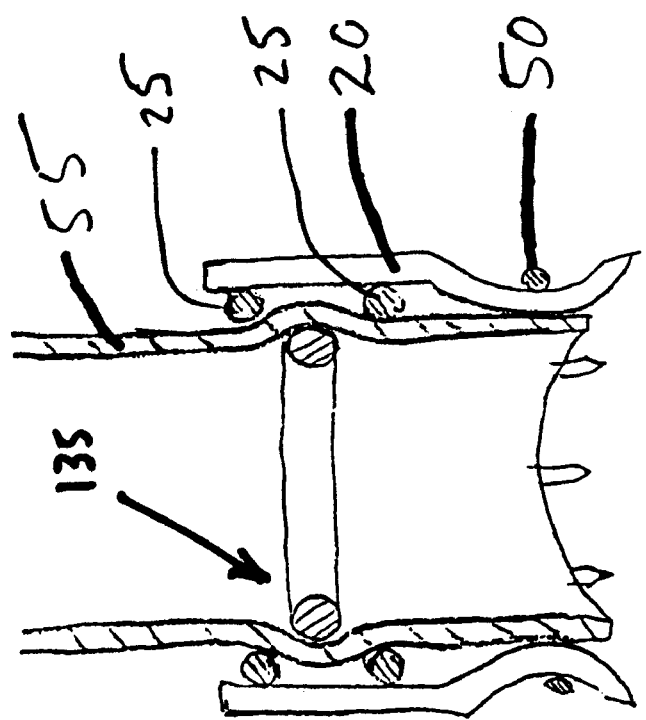
FIG. 20 illustrates an external version of a crown.

An alternative embodiment of the invention, as shown in FIG. 20, includes an apparatus and method to place vessel 55 inside crown 15 and to secure crown 15 with an internal lock ring 135 placed in vessel 55 at a position between two crown rings 25. Lock ring 135 exerts an outward force to hold vessel 55 to crown 15.

FIGS. 21A–21F show another embodiment of an apparatus and method to use metal suture wires to form an anastomotic connection between vessel 55 and vessel 65. A flexible mandrel 140 with a flanged end 145 is inserted into vessel 55 such that the end of vessel 55 is flared against flanged end 145 of mandrel 140.

A main body section 150 is placed over vessel 55. Section 150 consists of a tubular section 155 with a flanged end 160 that mates with that of flexible mandrel 140. Starting within flanged end 160 of the main body, and extending along the axial length a short distance, are wire tubes 165 that contain short pieces of metallic wire 170. Above tubes 165 is a sleeve 175 that slides along the outside of main body 150. Within the walls of sleeve 175 are receiving holes 180 for wire tubes 165, and plungers 185 extending from the receiving holes 180. Receiving holes 180, in combination with wire tubes 165, form a telescoping tube pair 190 that supports wire 170 as the end of the sleeve side is advanced forward. Sliding sleeve 175 toward flanged end 160 of main body 150 causes the plungers 185 to push wires 170 downward and into the tissue of vessel 55. Wire 170 would normally buckle under the load, but tubes 190 provide lateral support. When the tips of the wire 170 reach flanged end 145 of flexible mandrel 140, a die surface 195 (shown in FIG. 23B) deflects wire 170 outward and backward, i.e. proximally. At this point the tips of wire 170 have pierced the wall of vessel 55 and the wall of vessel 65 and, with the deflection caused by die surface 195, will now go back up through and out the wall of vessel 65 as sleeve 175 is advanced further. Wire advance is stopped when the outer wire tube 190 hits the bottom of receiving holes 180 of sleeve body 175. Main body 150 is then pulled away from the suture site along the vessel axis, allowing wires 170 to remain where they have been placed.

FIGS. 22A–22D show four possible end configurations for the tip of wire 170 to maintain the approximation of the tissue. If wire 170 is made of a very elastic material such as Nitinol, wire 170 can be preformed into these shapes and resume these shapes once it has been pushed out of wire tubes 165. Wire 170, as shown in FIGS. 22A, 22C, and 22D, holds the tissue in place because the tissue would otherwise have to bend wire 170 to provide an exit path. The distal end of wire 170, as shown in FIG. 22B, forms a loop about a section of the proximal strand, or vice versa, thereby creating an even more secure hold on the tissue.

In the case of malleable metallic suture wire 170, the section of suture wires 170 that have passed through die surface 195 can be formed into various shapes depending on the geometry of die surface 195. The smaller the radius of die surface 195, the tighter the curvature of the end configuration of suture wire 170. See FIGS. 23A–23F.

Because both main body 150 and sleeve 175 are circumscribing vessel 55 after it has been sutured, a method to remove main body 150 and sleeve 170 after the sutures have been placed is provided. Embodiments of main body 150 and sleeve 175 that have been split lengthwise and hinged at one edge are shown in FIG. 24A. After wire sutures 170 have been placed, sleeve 175 is opened up and pulled away, followed by main body 150 in the same fashion.

Flexible mandrel 140 must also be removed once the connection has been made. FIGS. 25A and 25B show flexible mandrel 140 that has an inflatable flanged end 200 with die surfaces 195 that expand with the inflation. The fluid pressure to expand mandrel 140 comes from a catheter 210 that is also used to deliver fluid from a point somewhere in the body or outside the body. Because die surfaces 195 need to be rigid, die surfaces 195 are placed on a separate surface 220 from flange 200 that can expand but also remain rigid to deflect wire 170.

The present devices provide a means of placing and securing wire sutures around the circumference of vessels during an anastomosis.

What is claimed is:

1. An apparatus for placing multiple sutures during anastomosis of physiological vessels, said apparatus comprising:
   a crown comprising:
      a plurality of strands, each strand of said plurality of strands having a first end and a second end, said strand first ends defining a first portion of said crown and said strand second ends defining a second portion of said crown;
      at least one circular band joining together said plurality of strands adjacent said first ends of said strands;
      each said strand forming a point at said second end thereof; and
      each said strand forming a hook adjacent said second end thereof for attachment to at least one physiological vessel;
   means for retaining each said hook in a first position for insertion of said second portion of said crown into physiological vessel; and
   means for deploying each said hook from said first position to a second position for securing each said hook to the physiological vessel;
   wherein said retaining means comprises a retaining ring, and said deploying means comprises removability of said retaining ring.

2. The apparatus of claim 1 wherein said removability of said retaining ring comprises severability by cutting said retaining ring.

3. A method for placing multiple sutures during anastomosis of physiological vessels, said method comprising:
   providing a crown comprising:
      a plurality of strands, each strand of said plurality of strands having a first end and a second end,
      at least one circular band joining together said plurality of strands adjacent said first ends of said strands; and each said strand forming a hook adjacent said second end of said strand with a point at said second end of said strand;

attaching a first physiological vessel to said crown by placing said first vessel within said crown and everting one end of said first vessel over said hooks; and attaching a second physiological vessel to said crown such that said first physiological vessel and said second physiological vessel are substantially joined to one another.

4. A crown for surgical formation of an anastomosis, the crown comprising:

an end ring;

a plurality of strands fixed to an inside surface of said end ring proximate a first end of said strands, and spaced from an outside surface of said end ring, and extending normal to said end ring; and each of said strands having a curved second end portion providing a distal end extending outwardly, the distal end being pointed;

wherein said strands are of substantially equal length and the pointed ends are disposed in a circle disposed concentrically outwardly from said end ring.

5. The crown in accordance with claim 4 and comprising a second ring spaced from said end ring, said strands being fixed to an inside surface of said second ring, and spaced from an outside surface of said second ring, and extending normal to said second ring.

6. The crown in accordance with claim 5 wherein said end ring and said second ring are of equal inside and outside diameters.

7. The crown in accordance with claim 4 wherein said strand distal pointed ends extend generally toward the first end.

8. The crown in accordance with claim 6 and comprising a retaining ring mounted on the strand curved second end portions to restrain outward movement of said strand distal ends.

9. The crown in accordance with claim 8 wherein said retaining ring is severable to permit the outward movement of said strand distal ends.

10. The crown in accordance with claim 5 wherein each of said strands is provided with a bend between said second ring and the second end portion, to provide flexibility in said strands.

11. The crown in accordance with claim 5 wherein each of said strands is provided with a coil spring portion between said second ring and the second end portion, to provide flexibility in said strands.

12. The crown in accordance with claim 4 wherein each of said strands is attached to said end ring by a spring structure.

13. A crown for surgical formation of an anastomoris, the crown comprising:

a plurality of rings having substantially equal inside and outside diameters;

a plurality of strands fixed to an inside surface of each of said rings and spaced from an outside surface of each of said rings; and each of said strands having curved first and second end portions providing first and second distal ends extending outwardly, the distal ends being pointed;

wherein said strands are of substantially equal length and the pointed ends are disposed in circles disposed concentrically outwardly from said rings.

14. The crown in accordance with claim 13, wherein said strand first end portion distal pointed ends and said strand second end portion distal pointed ends extend generally toward each other.

* * * * *